United States Patent
Warfield et al.

(10) Patent No.: US 10,317,498 B2
(45) Date of Patent: Jun. 11, 2019

(54) METHODS AND APPARATUS FOR MODELING DIFFUSION-WEIGHTED MR DATA ACQUIRED AT MULTIPLE NON-ZERO B-VALUES

(71) Applicant: Children's Medical Center Corporation, Boston, MA (US)

(72) Inventors: Simon K. Warfield, Brookline, MA (US); Benoit Scherrer, Cambridge, MA (US); Maxime Taquet, Nivelles (BE)

(73) Assignee: Children's Medical Center Corporation, Boston, MA (US)

( * ) Notice: Subject to any disclaimer, the term of this patent is extended or adjusted under 35 U.S.C. 154(b) by 271 days.

(21) Appl. No.: 15/022,343

(22) PCT Filed: Sep. 19, 2014

(86) PCT No.: PCT/US2014/056582
§ 371 (c)(1),
(2) Date: Mar. 16, 2016

(87) PCT Pub. No.: WO2015/042416
PCT Pub. Date: Mar. 26, 2015

(65) Prior Publication Data
US 2016/0231410 A1 Aug. 11, 2016

Related U.S. Application Data

(60) Provisional application No. 61/880,473, filed on Sep. 20, 2013.

(51) Int. Cl.
*G01R 33/563* (2006.01)
*G01R 33/56* (2006.01)
*A61B 5/055* (2006.01)

(52) U.S. Cl.
CPC ........ *G01R 33/56341* (2013.01); *A61B 5/055* (2013.01); *G01R 33/5608* (2013.01); *A61B 2576/026* (2013.01)

(58) Field of Classification Search
CPC .............. A61B 5/055; A61B 2576/026; G01R 33/56341; G01R 33/5608
See application file for complete search history.

(56) References Cited

U.S. PATENT DOCUMENTS

2005/0007100 A1* 1/2005 Basser ............. G01R 33/56341
324/200
2005/0068031 A1 3/2005 Frank
(Continued)

OTHER PUBLICATIONS

International Search Report and Written Opinion for Application No. PCT/US2014/056582 dated Dec. 16, 2014.
(Continued)

*Primary Examiner* — Patrick Assouad
*Assistant Examiner* — Haidong Zhang
(74) *Attorney, Agent, or Firm* — Wolf, Greenfield & Sacks, P.C.

(57) ABSTRACT

Methods and apparatus for characterizing biological micro structure in a voxel based, at least in part, on a set of diffusion-weighted magnetic resonance (MR) data. A multi-compartment parametric model is used to predict a diffusion signal for the voxel using information from the set of diffusion-weighted MR data. Predicting the diffusion signal comprises determining, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model. At least one first dataset of the set of diffusion-weighted MR data is associated with a first non-
(Continued)

zero b-value and at least one second dataset of the set of diffusion-weighted MR data is associated with a second non-zero b-value different than the first non-zero b-value.

16 Claims, 14 Drawing Sheets

(56) References Cited

U.S. PATENT DOCUMENTS

| | | | |
|---|---|---|---|
| 2008/0272781 | A1 | 11/2008 | Chiang et al. |
| 2009/0096448 | A1 | 4/2009 | Meredith et al. |
| 2011/0085722 | A1 | 4/2011 | Feiweier |
| 2012/0027283 | A1* | 2/2012 | Lang ............... A61B 6/469 382/132 |
| 2012/0062229 | A1 | 3/2012 | Topgaard |
| 2012/0194189 | A1* | 8/2012 | Sun ................. G01R 33/50 324/309 |
| 2012/0280686 | A1 | 11/2012 | White et al. |
| 2015/0253410 | A1 | 9/2015 | Warfield et al. |

OTHER PUBLICATIONS

International Preliminary Report on Patentability for Application No. PCT/US2014/056582 dated Mar. 31, 2016.

International Search Report and Written Opinion for International Application No. PCT/US2013/062230 dated Mar. 11, 2014.

International Preliminary Report on Patentability for International Application No. PCT/US2013/062230 dated Apr. 9, 2015.

Yeh et al., Reduced Encoding Diffusion Spectrum Imaging Implemented With a Bi-Gaussian Model. IEEE Transactions on Medical Imaging. 2008;27(10):1415-24.

Kuo et al., Optimization of diffusion spectrum imaging and q-ball imaging on clinical MRI system. NeuroImage. 2008;41(1):7-18.

Nezamzadeh et al., In-vivo investigation of the human cingulum bundle using the optimization of MR diffusion spectrum imaging. European Journal of Radiology. 2010;75(1):e29-36.

Peled et al., High b-Value Apparent Diffusion-Weighted Images From CURVE-Ball DTI. Journal of Magnetic Resonance Imaging. 2009;30(1):243-48.

Scherrer et al., Characterizing Complex White Matter Structure from Cube and Sphere Diffusion Imaging with a Multi-Fiber Model (CUSP-MFM). Proc. Intl. Soc. Mag. Reson. Med. 2011;19:1920.

Scherrer et al., Parametric Representation of Multiple White Matter Fascicles from Cube and Sphere Diffusion MRI. PLOS ONE. 2012;7(11):e48232.

Cook et al., Optimal Acquisition Orders of Diffusion-Weighted MRI Measurements. Journal of Magnetic Resonance Imaging. 2007;25(5):1051-58.

* cited by examiner

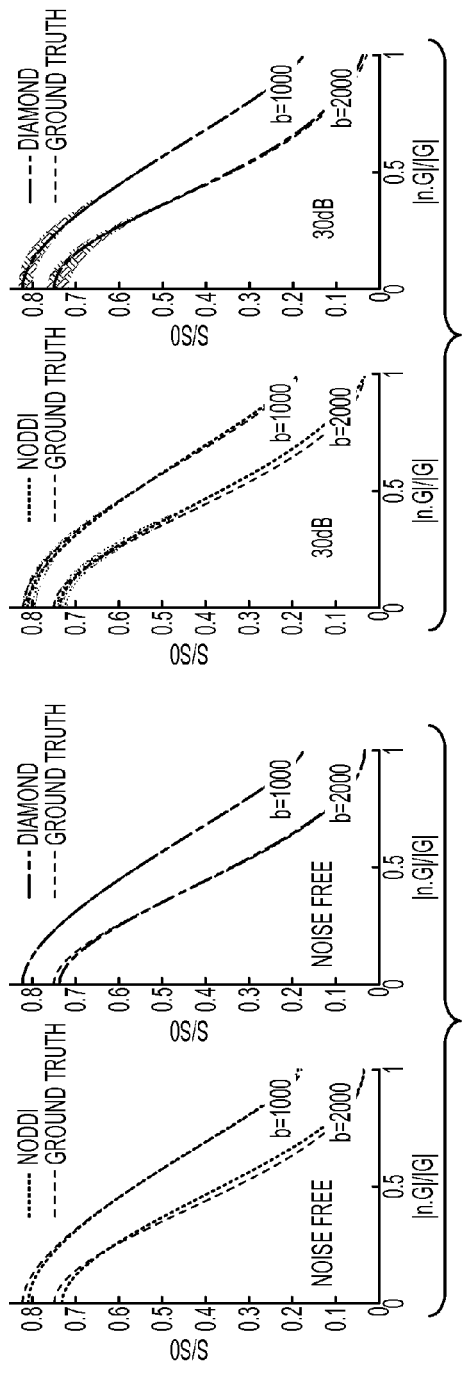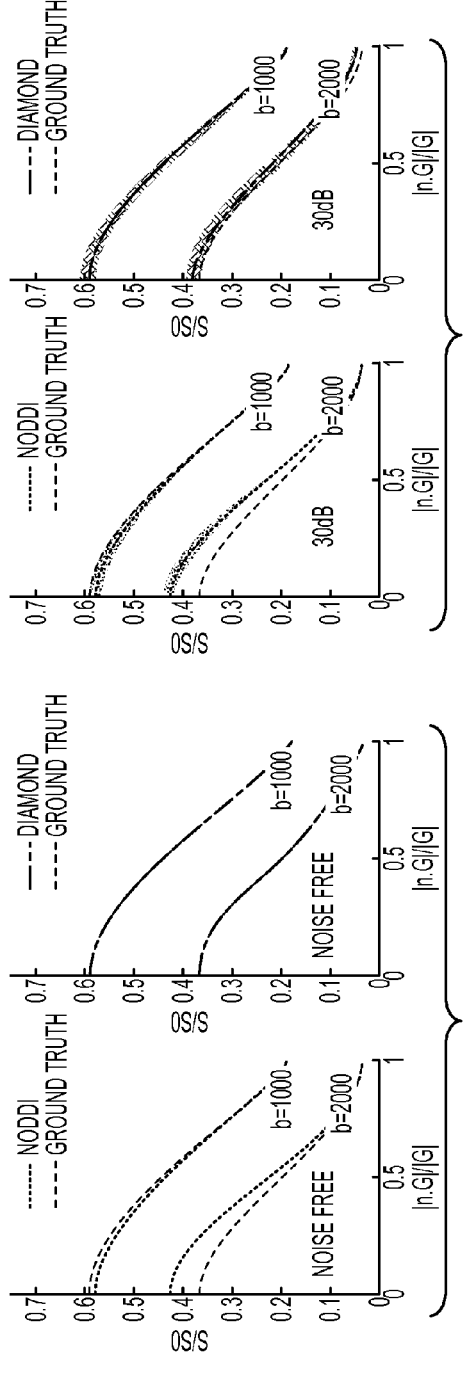
FIG. 6A  FIG. 6B  FIG. 6C  FIG. 6D

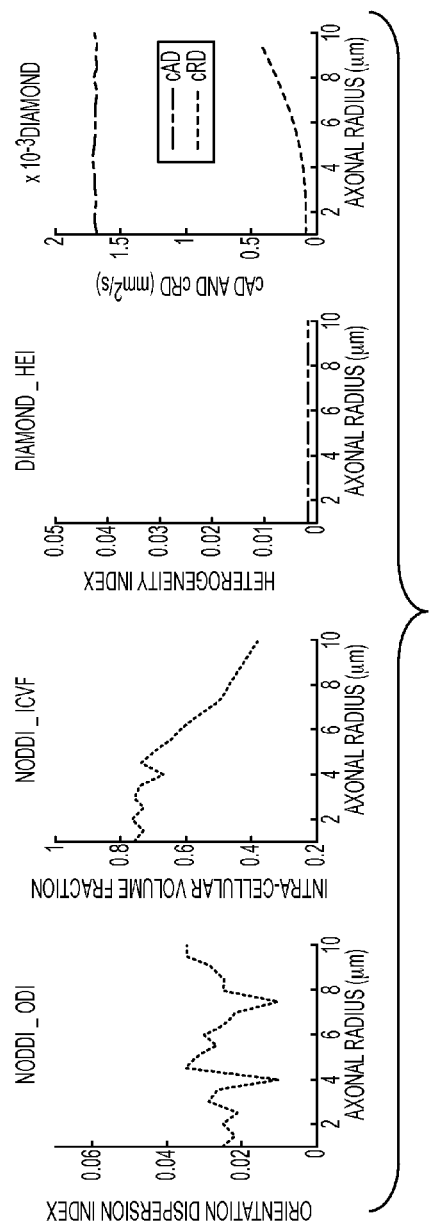
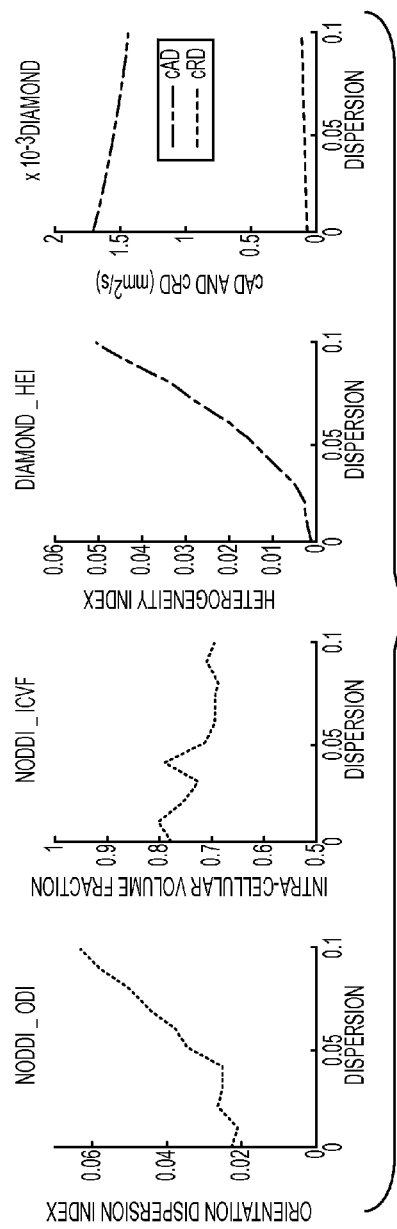
FIG. 7A
FIG. 7B

FIG. 9B $f_{iso}$

FIG. 9D $f_1$

METHODS AND APPARATUS FOR MODELING DIFFUSION-WEIGHTED MR DATA ACQUIRED AT MULTIPLE NON-ZERO B-VALUES

RELATED APPLICATIONS

This Application is a national stage filing under 37 U.S.C. § 371 of International Application No. PCT/US2014/056582, filed Sep. 19, 2014, entitled "METHODS AND APPARATUS FOR MODELING DIFFUSION-WEIGHTED MR DATA ACQUIRED AT MULTIPLE NON-ZERO B-VALUES," which claims priority under 35 U.S.C. § 119(e) to U.S. Provisional Patent Application Ser. No. 61/880,473 filed Sep. 20, 2013, each of which is incorporated by reference in its entirety.

BACKGROUND

Magnetic resonance imaging (MRI) includes techniques for capturing data related to the internal structure of an object of interest, for example, by non-invasively obtaining images of internal structure of the human body, and has been widely used as a diagnostic tool in the medical community. MRI exploits the nuclear magnetic resonance (NMR) phenomenon to distinguish different structures, phenomena or characteristics of an object of interest. For example, in biological subjects, MRI may be employed to distinguish between various tissues, organs, anatomical anomalies (e.g., tumors), and/or to image diffusion, blood flow, blood perfusion, etc.

In general, MRI operates by manipulating spin characteristics of subject material. MRI techniques include aligning the spin characteristics of nuclei of the material being imaged using a generally homogeneous magnetic field and perturbing the magnetic field with a sequence of radio frequency (RF) pulses. To invoke the NMR phenomenon, one or more resonant coils may be provided proximate an object positioned within the magnetic field. The RF coils are adapted to generate RF pulses, generally in the form of RF pulse sequences adapted for a particular MRI application, to excite the nuclei and cause the spin to process about a different axis (e.g., about an axis in the direction of the applied RF pulses). When an RF pulse subsides, spins gradually realign with the magnetic field, releasing energy that can be measured to capture NMR data about the internal structure of the object.

Measuring water diffusion with magnetic resonance diffusion-weighted imaging (MR-DWI) enables probing tissue at a length scale much smaller than the image spatial resolution. This has enabled non-invasive investigation and characterization of the white matter architecture and microstructure in the brain. In particular DWI enables investigation of the brain microstructure by probing natural barriers to diffusion in tissues. Diffusion in white matter fascicles has been observed to be highly anisotropic, with primary orientation of the diffusion corresponding to the orientation of the fascicle. The underlying microstructure that gives rise to this anisotropy has been investigated. Diffusion tensor imaging (DTI) was proposed to describe the three-dimensional nature of anisotropic diffusion. Assuming homogeneous Gaussian diffusion within each voxel, DTI describes the magnitude and orientation of water molecule diffusion with a second-order tensor estimated from diffusion measurements in several directions. More precisely, DTI relates the measured diffusion-weighted signal $S_k$, along a gradient direction $g_k$ to the non-attenuated signal $S_0$ via the Stejskal-Tanner equation:

$$S_k(D) = S_0 e^{-TE/T2} e^{-\gamma^2 \delta^2 (\Delta - \delta/3) g_k^T D g_k}, \quad (1)$$

where TE is the echo time, T2 is the T2 relaxation time of the tissue, $\gamma$ is the gyromagnetic ratio, $\delta$ and $\Delta$ are the diffusion sensitizing pulse gradients duration and time separation, and D is the 3×3 diffusion tensor.

The applied b-value defined by $b_k = \gamma^2 \delta^2 (\Delta - \delta/3) G_k^2$, which depends on the gradient strength $G_k^2 = \|g_k\|^2$, has been introduced to simplify the notations in equation (1) and describes the diffusion sensitization strength. The nominal b-value $b_{nominal} = \gamma^2 \delta^2 (\Delta - \delta/3)$ describes the b-value for the unit-norm gradients. The term $e^{-TE/T2}$ is generally considered constant across all gradients and omitted. However, and importantly, this term highlights how the signal amplitude $S_k(D)$ decreases exponentially for increasing TE.

DTI and its underlying mono-exponential signal attenuation assumption are generally considered to satisfactorily represent single fascicles when imaging with b-values lower than 3000 s/mm², which is frequently the case in clinical settings. Non-monoexponential behavior of the signal at a voxel in this b-value range can arise from cerebral spinal fluid (CSF) partial voluming, mixtures of fascicles present in the voxel, and other sources. The diffusion tensor enables representation of the orientation of a single fascicle, as well as the characterization of the diffusion process. Tensor parameters such as the fractional anisotropy (FA), the mean diffusivity (MD), the axial diffusivity (AD), and the radial diffusivity (RD) can be computed, and have been shown to provide valuable information that reflects changes in the white matter due to development, disease and degeneration. DTI requires relatively short acquisition times and has been successfully employed in clinical studies.

DTI has been shown to be a poor parametric model for representing the diffusion signal arising at voxels that encompass multiple fascicles with heterogeneous orientation such as fascicle crossing, kissing or fanning. Several approaches have been investigated to overcome this fundamental limitation, which involve various diffusion signal sampling schemes and ways to analyze the diffusion signal as detailed below.

Cartesian sampling and spherical sampling are two q-space sampling strategies that have been used for complex fiber structure assessment. Cartesian sampling is used by diffusion spectrum imaging (DSI). Spherical sampling as employed in high angular resolution imaging (HARDI) techniques reduces the imaging time and requires imaging gradients with moderate intensity. Several HARDI-based techniques have been proposed, as discussed in further detail below. Single-shell HARDI acquisitions with a single non-zero b-value have been considered to image a sphere of constant radius in q-space. Multiple-shell HARDI acquisitions that enable the acquisition of multiple non-zero b-values by combining in a single acquisition, the sampling of multiple shells of different radius in q-space, have also been proposed.

Other sampling techniques have been proposed for reasons other than assessing complex fiber structures. For example, sampling using the tetrahedral $\sqrt{3}$-norm gradients has been employed to measure the apparent diffusion coefficient (ADC) from four diffusion measurements. Because $b_k = b_{nominal} G_k^2$, this technique enables imaging at higher b-values than the nominal b-value without modifying the timing parameters $\delta$ and $\Delta$, but by using gradients with norm greater than one. It provides the optimal minimum achievable TE for the corresponding applied b-value, leading to a better SNR and potentially to lower eddy current distortion because the diffusion gradient pulses can be shortened. Using the same concept, the six hexahedral $\sqrt{2}$-norm gradients may be used to estimate a diffusion tensor from seven measurements. Furthermore, in (CUbe Rays to Vertices and Edges) CURVE-ball, a spherical sampling and the hexahedral and tetrahedral gradients are combined to perform the estimation of a single-tensor model at three different diffusion scales $b_{nominal}$, $2b_{nominal}$, and $3b_{nominal}$.

Several approaches have been investigated to analyze the diffusion signal and represent multiple white-matter fascicles with complex geometry. Both parametric (model-based) and non-parametric (model-free) approaches have been proposed. Generally, these models focus on estimating either (1) the diffusion displacement probability density function (diffusion PDF), (2) the diffusion orientation distribution function (dODF) which is the angular profile of the diffusion PDF or (3) the fiber orientation distribution function (fODF), also known as the fiber orientation density (FOD) and which is of central interest for tractography.

Model-free approaches include diffusion spectrum imaging (DSI). In this technique, the diffusion PDF is directly estimated from the inverse Fourier transform of the measured signal, requiring a very high number of measurements to satisfy the Nyquist condition. Q-ball imaging (QBI) estimates an approximate non-parametric angular profile of the diffusion PDF without actually computing the diffusion PDF, by using the Funk-Radon transform. Fast and robust analytical QBI estimation procedures have been proposed. QBI results in the estimation of an approximated dODF related to the true dODF by modulation with a zero-order Bessel function. This leads to a spectral broadening of the diffusion peaks of individual fascicles at moderate b-values accessible on a clinical scanner, perturbing the FOD reconstruction necessary for carrying out tractography. Mixing of individual tracts in a voxel leads to local maxima that does not coincide with the true fascicle orientation, leading to a relatively low fidelity representation. To avoid the usual Q-Ball approximation, an Exact Q-Ball Imaging (EQBI), which derives a direct relationship between the dODF and the diffusion data has been proposed. EQBI enables the estimation of the exact dODF under the assumption of a Gaussian profile.

Q-space approaches such as DSI, QBI, or EQBI are limited by at least three error sources. These techniques are based on the narrow pulse approximation assumption, considering that molecules do not diffuse during the application of the diffusion sensitizing gradients. The gradient pulses are then modeled by a Dirac shape which is not practically feasible, especially on clinical systems. In practice, in clinical settings, the diffusion-encoding gradient duration $\delta$ is typically of the same order of magnitude as the time offset $\Delta$ between encoding gradients ($\Delta/\delta \approx 1$) to minimize T2 decay and to obtain better SNR, which is a very poor approximation of a Dirac shape. Additionally, since the imaging time has to be finite, only a finite region in q-space is imaged using these techniques. This has been shown to lead to a blurred propagator with decreased contrast and angular resolution. Also, these techniques are limited by the need to truncate the Fourier representation which is required to numerically compute the infinite series involved in the Fourier transformation, leading to quantization artifacts.

In contrast, parametric models describe a predetermined model of diffusion rather than an arbitrary one. They potentially require a smaller number of images to be acquired, leading to a reduced acquisition time. Several model-based approaches have been investigated. Among them, generalized diffusion tensor imaging (GDTI) models the white-matter fascicles with higher-order tensors; spherical deconvolution (SD) directly estimates the FOD instead of the dODF and has a better angular resolution; and diffusion orientation transform (DOT) employs a model-based q-space modeling based on the assumption of a monoexponential decay of the signal attenuation.

SUMMARY

Some embodiments include a system for characterizing biological microstructure in a voxel based, at least in part, on a plurality of diffusion-weighted images. The system comprises at least one computer processor and at least one storage device configured to store a plurality of instructions that, when executed by the at least one computer processor, perform a method of fitting a novel parametric model using information from a set of diffusion-weighted data.

In some embodiments, the novel parametric model describes statistical distributions of 3-D diffusivity arising from each of a plurality of tissue compartments for the voxel. The complexity of the parametric model may be increased by adapting the parametric model to account for additional compartments, such that the parametric model is capable of modeling parameters for the set of diffusion-weighted data from one to N compartments. According to some embodiments, the first compartment models free or restricted isotropic diffusion, and at least one subsequent compartment models restricted or hindered anisotropic diffusion by assuming presence of one or more white matter fascicles in the voxel.

According to some embodiments, fitting the parametric model comprises determining, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model, wherein at least one first dataset of the set of diffusion-weighted MR data is associated with a first non-zero b-value and at least one second dataset of the set of diffusion-weighted MR data is associated with a second non-zero b-value different than the first non-zero b-value.

Some embodiments include determining the number of compartments to be modeled by the parametric model by minimizing a generalization error resulting from using the parametric model with N−1 compartments and selecting the parametric model with the number of compartments with the smallest generalization error. As a result, the parametric model utilized for a given voxel may be adapted according to the number of white matter fascicles believed to be present in the voxel such that the complexity of the model fits the microstructure within the voxel appropriately.

Some embodiments are directed to a computer system for characterizing biological microstructure in a voxel based, at least in part, on a set of diffusion-weighted magnetic resonance (MR) data. The computer system comprises at least one computer processor and at least one storage device configured to store a plurality of instructions that, when executed by the at least one computer processor, perform a method. The method comprises fitting a parametric model using information from the set of diffusion-weighted MR data, wherein the parametric model is a multi-compartment model, and wherein fitting the parametric model comprises determining for the voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model, wherein at least one first dataset of the set of diffusion-weighted MR data is associated with a first non-zero b-value and at least one second dataset of the set of diffusion-weighted MR data is associated with a second non-zero b-value different than the first non-zero b-value, and outputting an indication of the first set of parameters and/or the second set of parameters for the voxel.

Some embodiments are directed to a method of characterizing biological microstructure based, at least in part, on a set of diffusion-weighted magnetic resonance (MR) data. The method comprises receiving the set of diffusion-weighted MR data, wherein at least one first dataset of the set of diffusion-weighted MR data is associated with a first non-zero b-value and at least one second dataset of the set of diffusion-weighted MR data is associated with a second non-zero b-value different than the first non-zero b-value; fitting, by at least one computer processor, a parametric model using information from the set of diffusion-weighted MR data, wherein the parametric model is a multi-compartment model, and wherein fitting the parametric model comprises determining for a voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model; and outputting an indication of one or more of the at least one first diffusion parameter and one or more of the at least one second diffusion parameter for the voxel.

Some embodiments are directed to a non-transitory computer readable storage medium encoded with a plurality of instructions that, when executed by at least one computer processor, perform a method. The method comprises fitting a parametric model using information from the set of diffusion-weighted MR data, wherein the parametric model is a multi-compartment model, and wherein fitting the parametric model comprises determining for a voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model, wherein at least one first dataset of the set of diffusion-weighted MR data is associated with a first non-zero b-value and at least one second dataset of the set of diffusion-weighted MR data is associated with a second non-zero b-value different than the first non-zero b-value; and outputting an indication of one or more of the at least one first diffusion parameter and one or more of the at least one second diffusion parameter for the voxel.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7 shows plots of parameters for various microstructures determined using variations of the NODDI model and a novel DIAMOND model used in accordance with some embodiments;

DETAILED DESCRIPTION

Figure 1A:
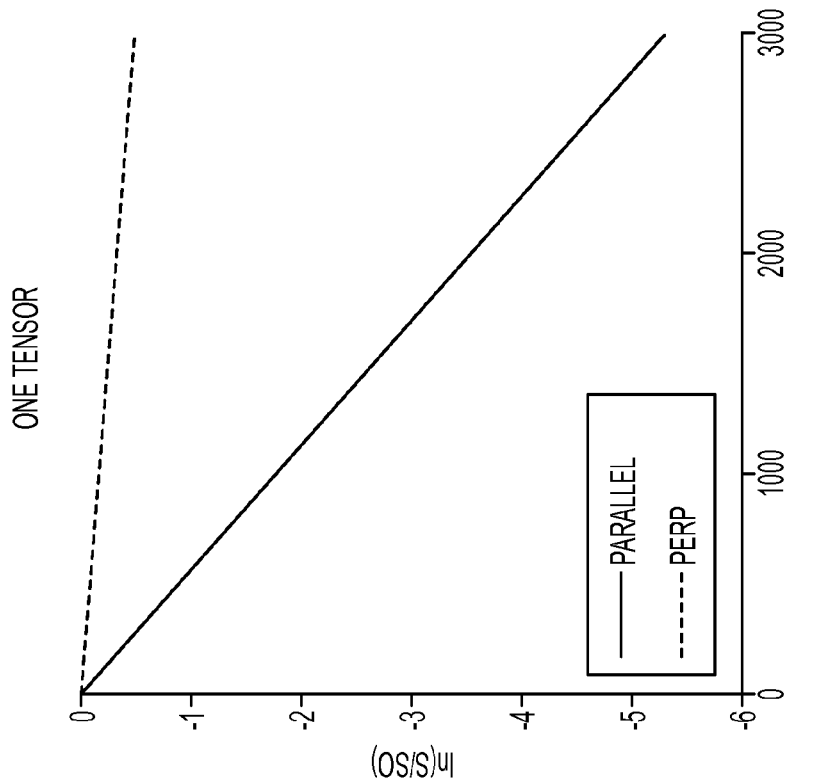
FIG. 1 illustrates the concept of non-monoexponential decay of signal with b-value detected in a voxel in a multi-fascicle model.

Following below are more detailed descriptions of various concepts related to, and inventive embodiments of, methods and apparatus according to the present disclosure for fitting a parametric model to a set of diffusion-weighted images having multiple non-zero b-values. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

A drawback of several of the diffusion-based modeling techniques described above (e.g., DSI, QBI, DOT, SD, and GDTI) is that they focus on describing the general shape of the diffusion profile in each voxel. They do not represent each fascicle independently and therefore do not characterize the proportion of each fascicle passing through a voxel. Importantly, they do not enable characterization of each fascicle. Diffusion parameters such as the generalized fractional anisotropy (GFA) can be computed, but represent a DW signal dispersion property rather than an individual fascicle property. For example, a synthetic fascicle consisting of an identical tensor at every voxel crossed by another synthetic fascicle has a GFA that varies in the crossing region, which is not clinically relevant. Using the techniques described above, it is generally not possible to distinguish whether a change in diffusion parameters along a fascicle is associated with a change in the intrinsic fascicle property or because of the presence of crossing fascicles. These approaches provide information about the distribution of fascicle orientations in the voxel but are limited to connectivity assessment.

In contrast, multi-fascicle models (MFM) consider, at each voxel, a mixture of independent fascicles with heterogeneous orientation. Making the assumption of a slow exchange between the fascicles' compartments, the diffusion signal in each voxel is modeled as a mixture of the diffusion signal arising from each individual fascicle. Integration of an isotropic component has also been investigated to model the diffusion of unrestricted water. This enables characterization of pathologies such as edema, stroke, or inflammation. This also enables characterization of the CSF contamination due to partial volume effect, known to perturb the accurate estimation of the anisotropic diffusion compartments. Ultimately, the diffusion-weighted signal $S_k$ along a gradient direction $g_k$ for MFM with an isotropic compartment and $N_f$ fascicles can be described by the following general mixture;

$$S_k(D, f) = S_0 \left( f_0 S_k^{free\_water} + \sum_{j=1}^{N_f} f_j S_{k,j}^{single\_fascile} \right), \quad (2)$$

where $S_{k,j}^{single\_fascile}$ is the diffusion signal arising from a single fascicle, $S_k^{free\_water}$ is the diffusion signal arising from the unrestricted water diffusion, and $f=(f_0, \ldots, f_{N_f})$ describes the fractions of occupancy of each compartment ($f_j \in [0,1]$) and sum to one.

The diffusivity of free water is generally considered to be well modeled by an isotropic Gaussian distribution, leading to $S_k^{free\_water}=e^{-b_k D_{iso}}$, with $D_{iso}$ being the diffusivity of free water.

In a particular case of the multi-fascicle model called the "ball-and-stick" model, each individual fascicle is represented by a stick in the expression of $S_{k,j}^{single\_fascile}$. With this simplification, an essential advantage of multi-fascicle models is lost: the ball-and-stick model provides information only about the fascicles' orientation, but does not enable the assessment of fascicle properties such as the fascicle anisotropy and diffusivity, limiting the use of the ball-and-stick model to connectivity studies.

In contrast, since an individual fascicle is generally considered to be well represented by a single tensor in DTI, a natural candidate has been to represent each fascicle by a tensor. Considering $N_f$ tensors $D=(D_1, \ldots, D_{N_f})$ representing the $N_f$ fascicles, this amounts to setting $S_{k,j}^{single\_fascile}=e^{-b_k g_k^T D_j g_k}$ leading to the so-called multi-tensor model. The multi-tensor model has the fundamental advantage over other common representations of modeling each fascicle independently. It enables the assessment of individual fascicle characteristics by computing diffusion tensor parameters for each fascicle, which enables characterization of the white-matter appearance, changes and alterations, and enables comparison of diffusion characteristics between corresponding anatomical fascicles across individuals, which is of great interest for clinical applications. In addition, the full multi-tensor model estimation enables characterization of the fraction of occupancy for each fascicle, providing information about the mixing proportions and compensating for partial volume effect.

The spatial resolution of diffusion-weighted imaging (DWI) is typically on the order of 6-27 mm$^3$. As a result, the measured DW signal in each voxel combines the signal arising from a variety of microstructural environments including multiple cell types, sizes, geometries and orientations and extra-cellular space. A non-monoexponential decay may be observed in voxels when imaging with high b-values, providing evidence that the single tensor model and its underlying Gaussian assumption is not appropriate to accurately represent the diffusion signal in the voxel. The biophysical mechanisms responsible for the non-monoexponential behavior are, however, numerous and not completely understood. It is commonly recognized that compartmentalization of the voxel in different subregions with heterogeneous properties can lead to a non-monoexponential decay under certain acquisition conditions.

As illustrated in FIG. 1, mixing of an isotropic unrestricted water compartment with multiple anisotropic compartments, with each compartment being modeled with a purely monoexponential decay, leads to a non-monoexponential decay due to partial volume averaging, even at moderate b-values. At a smaller diffusion scale, the presence of intra- and extracellular compartments leads to a non-monoexponential decay for very high b-values, even for a single fascicle. Nevertheless, the presence of this phenomenon at clinically relevant b-values, with long diffusion sensitization pulse duration δ, long echo times and low signal-to-noise ratio remains unclear.

Figure 1B:
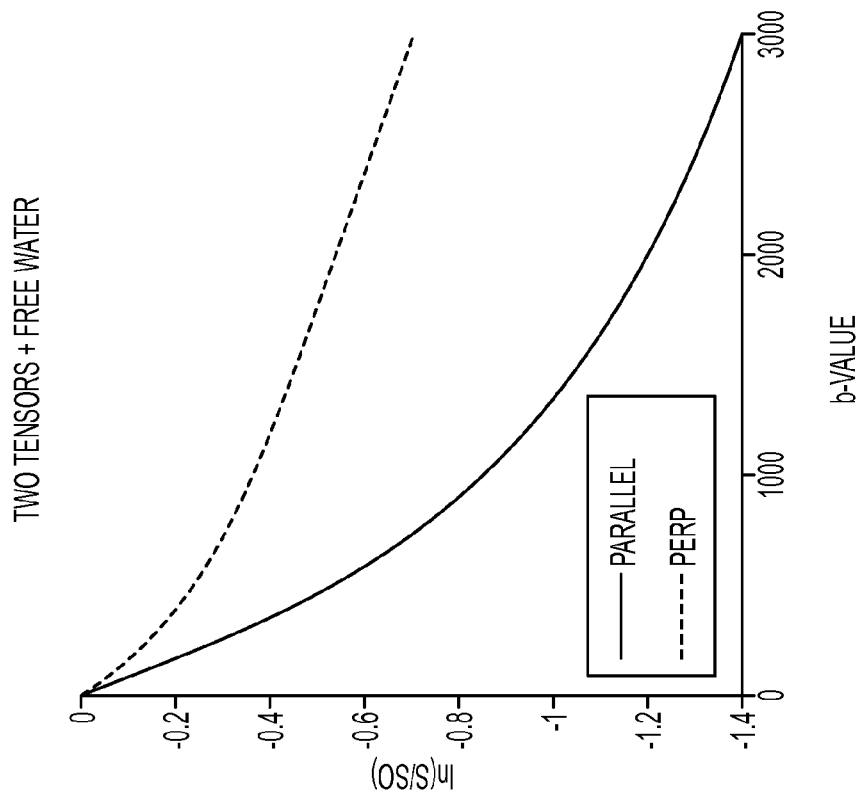

FIG. 1 illustrates that intra-voxel orientation heterogeniety and partial volume averaging leads to a non-monoexponential decay in a voxel. FIG. 1A illustrates the monoexponential decay arising from a single tensor (FA=0.9, diffusivity=2.1×10$^{-3}$ mm$^2$/s) as shown by the linearity of log(S/S0) in both the parallel and perpendicular directions with respect to the tensor orientation (noise-free case). FIG. 1B illustrates that mixing of an isotropic compartment ($f_0$=0.2, $D_{iso}$=3×10$^{-3}$ mm$^2$/s) and two crossing fascicles represented by two single tensors ($f_1$=$f_2$=0.4, FA=0.9, diffusivity=2.1×10$^{-3}$ mm$^2$/s, crossing angle=900) leads to a non-monoexponential decay in the voxel, even for b-values below 3000 s/mm$^2$. This illustrates that a non-monoexponential decay in a voxel may arise from a sum of monoexponential behaviors.

Models have been proposed to account for the observed non-monoexponential decay, including fitting a multi-exponential model and a "stretched-exponential model." The estimation of a Kurtosis term, which is a dimensionless measure of the deviation of the water diffusion profile from a Gaussian distribution, has also been investigated. These models attempt to describe the signal arising from each entire voxel and focus on capturing the mathematical deviation from the monoexponential decay.

Other "generative" models focus on modeling the biophysical mechanisms underlying the MR signal formation, and have parameters that reflect the tissue compartments present in each voxel. These so-called diffusion compartment models are based on underlying observations of the biological microstructure that alter the diffusion signal and are of great interest to characterize and compare tissue properties. For example, assessment of the isotropic diffusion arising from the extracellular space is useful to account for cerebrospinal fluid (CSF) due to partial volume effect and for the characterization of vasogenic edema, inflammation, and neurodegeneration. A model of the axonal dispersion is useful to capture information about the dendrite density. A model for each individual fascicle is useful to characterize the fascicle density, the axonal diameter distribution, or the myelin integrity. In this context, various diffusion compartment models have been proposed, giving rise to what may be referred to as "diffusion compartment imaging" (DCI) techniques. The inventors have recognized and appreciated that existing DCI techniques rely on assumptions that do not reflect known tissue microstructural properties, as discussed in more detail below.

An example of a DCI technique is the composite hindered and restricted model of diffusion (CHARMED), which represents the intra-axonal diffusion by the analytic expression for diffusion within impermeable cylinders and the extra-cellular hindered diffusion with a full tensor. CHARMED requires long acquisition times and very high b-values (up to 10000 s/mm$^2$), limiting its use in routine clinical practice.

Another DCI technique called neurite orientation dispersion and density imaging (NODDI) focuses on explicitly modeling the fascicle dispersion by a Watson distribution of sticks in each voxel. However, this is achieved at the cost of key assumptions that are inconsistent with known tissue microstructure. For example, the NODDI model relies on a prefixed representation of a white matter (WM) fascicle constant throughout the entire brain, while fascicles with various microstructures have been observed such as in the body of the corpus callosum. NODDI ignores the intra-axonal radial diffusivity and, similar to diffusion tensor imaging (DTI), assumes the presence of a single fascicle in each voxel while crossing fascicles occur in 60% to 90% of the voxels in the human brain.

Most prior implementations of the above-described techniques accounting for the non-monoexponential signal decay have considered the case of a single fascicle in each voxel. For example, when estimation of a single tensor and a single Kurtosis term with b-values as low as b=2500 s/mm$^2$ was used, a significant deviation from the Gaussian distribution was measured. However, as illustrated by FIG. 1, the intra-voxel orientation heterogeneity and partial volume effect may be the predominant sources of the observed non-monoexponential decay at such a diffusion scale. More precisely, while the presence of a non-monoexponential decay for an individual fascicle is commonly accepted when using very high b-values and a short gradient pulse duration δ, its presence in data acquired with a clinical scanner with limited b-value range and large remains unclear. Particularly, the non-monoexponential behavior may be negligible when considering b-values lower than b<3000 s/mm$^2$, and when the acquisition time or the available gradient strength is limited, a monoexponential per-fascicle model may be safely employed.

Figure 2C:
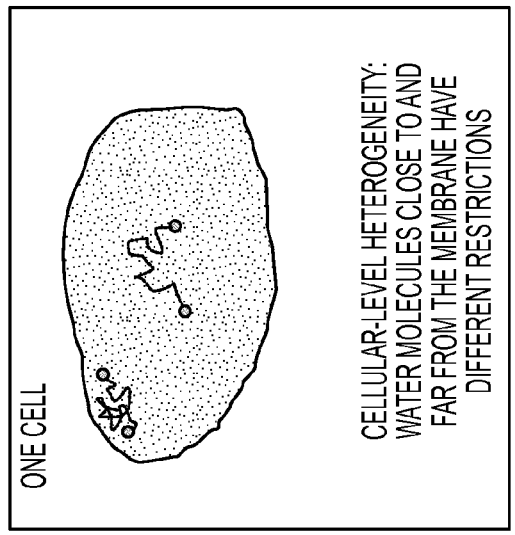
FIG. 2 illustrates multiple scales of intra-voxel heterogeneity that may be modeled in accordance with some embodiments.
Figure 2B:
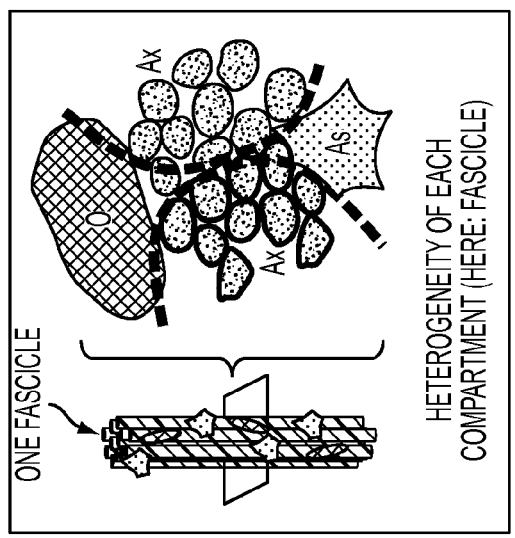
Figure 2A:
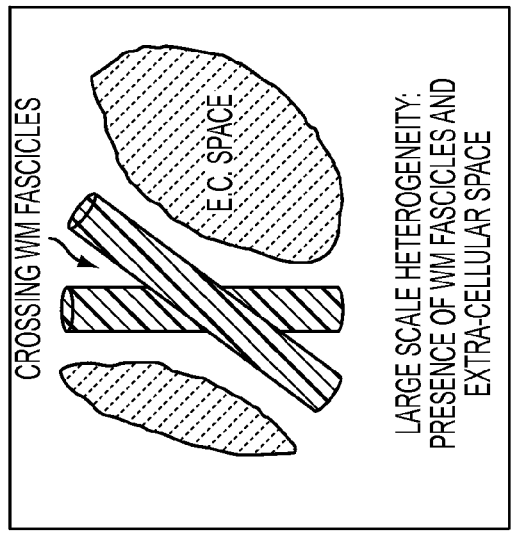

Some techniques provide a more detailed model of the tissue microstructure that gives rise to the signal attenuation. The observed non-monoexponential decay in each voxel likely arises from both large-scale and small-scale intra-voxel heterogeneities, as shown in FIG. 2. FIG. 2A illustrates that large-scale heterogeneity includes the mixing of large-scale microstructural environments (LSME), also referred to as compartments, such as the mixing of multiple WM fascicles with extra-cellular space. Large-scale heterogeneity also originates from partial volume averaging such as occurs when cerebrospinal fluid, gray matter and/or white matter are present in a voxel. FIG. 2B shows that each large-scale microstructural environment may contain a complex varying microstructure including axons with varying radii and degrees of myelination, or fascicles with a varying density of glial cells such as astrocytes and oligodendrocytes. It is likely that water molecules interacting with an homogeneous portion of this structure are well modeled by an exponential. However, the overall signal arising from the compartment may significantly deviate from a mono-exponential decay in the presence of heterogenity of the spin packets composing the compartment. FIG. 2C shows that at an even smaller scale, other biophysical mechanisms such as intracellular heterogeneities and the proximity of cell membranes may locally restrict water molecule motion and contribute to the signal decay behavior. For example, a non-monoexponential decay within the intracellular space of a single cell, the frog oocyte has been observed (Ax: axons with various degrees of myelination; As: Astrocyte; O: Oligodendrocyte).

Figure 3C:
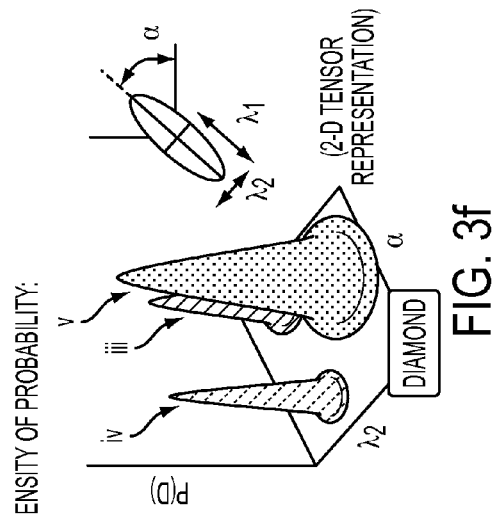
FIG. 3 schematically illustrates parametric model representations that account for intra-voxel heterogeneity in accordance with some embodiments.
Figure 3F:
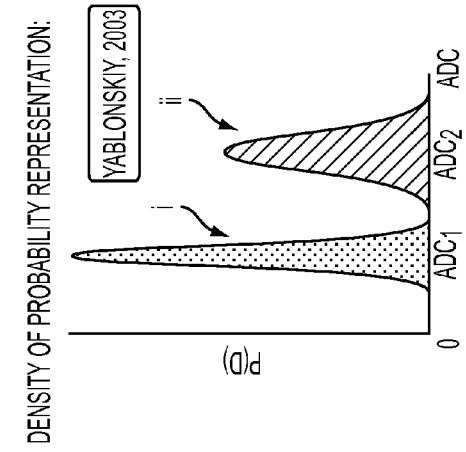
Figure 3B:
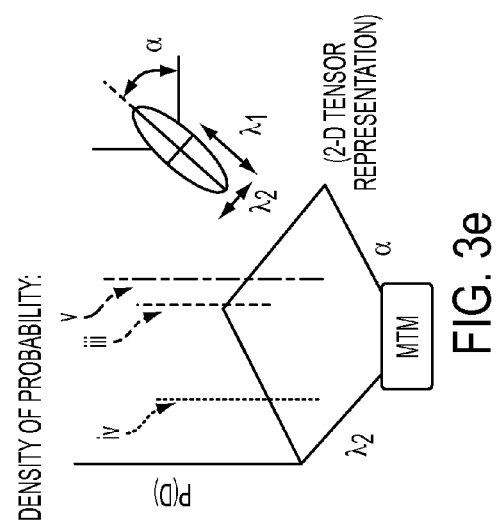
Figure 3E:
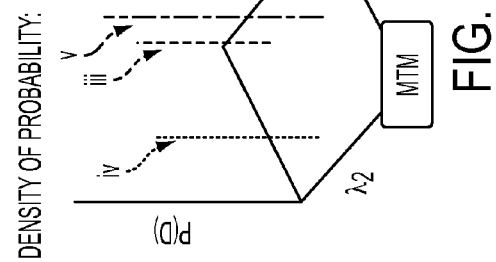
Figure 3A:
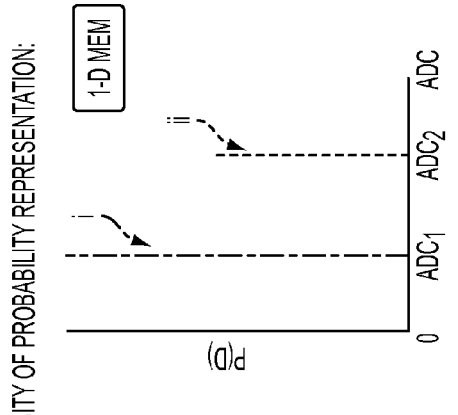

In the context of non-monoexponential decay arising from both large-scale and small-scale intra-voxel heterogeneities, a statistical model of the apparent diffusion coefficient (ADC) that intrinsically reflects the presence of heterogeneous microstructural environments in each voxel has been proposed. The model considers measurements arising from the large number of spin packets in each voxel such that each homogeneous spin packet undergoes local isotropic Gaussian diffusion described by an ADC D and proposes to model the DW signal by a distribution of the contributions of all spin packets as:

$$S_k = S_0 \int P(D) \exp(-b_k D) dD, \quad (3)$$

where $S_k$ is the measured diffusion signal for the b-value $b_k$, $S_0$ is the signal with no diffusion applied and P(D) is a probability distribution that describes the fraction of spin packets with an ADC D in the voxel, as shown in FIGS. 3a-c. This statistical model of the ADC reflects, via the shape of the scalar-valued distribution P(D), the overall diffusivity and heterogeneity in each voxel. Originally formulated as a mono-directional model, it was extended to the multi-directional case by estimating one ADC per direction. This model, however, cannot characterize the 3-D anisotropy of the diffusion observed in the brain and cannot describe the spin packets distribution of oriented 3-D large-scale microstructural environments such as WM fascicles.

FIG. 3a illustrates a hypothetical isotropic two-population (or two-compartment) environment. FIG. 3b shows that under the hypothesis of purely homogeneous compartments with no exchange, a bi-exponential decay is traditionally considered to describe the signal arising from the isotropic two-population environment of FIG. 3a. The probability density of diffusivities represents the fraction of all possible ADCs present in the voxel. For the bi-exponential model, the probability density of diffusivities consists of two Diracs representing the ADC of each compartment. FIG. 3c illustrates another technique in which each compartment is considered to have some degree of heterogeneity. In this technique, a peak-shaped continuous distribution of ADCs is used for each compartment, with the heterogeneity of a compartment being captured by the concentration of the corresponding peak.

In another approach, a 1-D gamma distribution model of diffusivities has been incorporated in the ball-and stick model, described above. In this approach, the sticks only model the parallel intra-axonal diffusivity for each fascicle and the gamma distribution is mostly used to improve the fitting and to reduce overfitting.

In accordance with some embodiments, a parametric model may predict the diffusion signal using four compartments to respectively represent 1) freely diffusing water, 3) isotropic restricted diffusion water, 3) water molecules restricted to the intra-axonal space and 4) water molecules hindered by axonal membranes. However, which parameterization best describes the non-monoexponential signal arising from each tissue compartment remains an open problem.

Figure 3D:
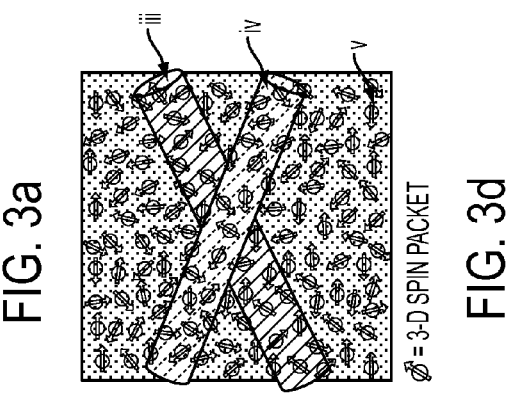

The inventors have recognized that equation (3) can be generalized by modeling the tridimensional diffusivity of each spin packet with a full diffusion tensor D, as shown in FIGS. 3d-f. However, this technique is analytically challenging because it implies the integration of a matrix-variate distribution P(D) over the space of tensors, which are symmetric positive-definite (SPD) matrices. In this context, a normal distribution for symmetric matrices, not restricted to SPD matrices has been proposed. In contrast, a natural distribution for SPD matrices is the matrix-variate Gamma (mv-Γ) distribution, which generalizes the Wishart distribution by allowing non-integer numbers of degrees of freedom. Some prior investigations have employed a mixture of N>100 Wishart distributions with fixed parameters and orientations uniformly distributed to discretize the unit sphere in a spherical deconvolution approach. Similarly to Q-Ball imaging and constrained spherical deconvolution (CSD), such an approach focuses on describing the orientation profile of the diffusion at a single b-value without explicitly modeling the tissue microstructure. Such approaches correspond to a model of the signal and do not provide insight into the tissue compartments giving rise to the signal.

FIG. 3d shows a hypothetical multi-compartment model, in which an isotropic (v) and two anisotropic (iv and iii) compartments are mixed. For illustration purposes a 2-D multi-compartment model is shown. FIG. 3e shows that under the hypothesis of purely homogeneous compartments with no exchange, a multi-tensor model is typically employed to describe the signal arising from environment of FIG. 3d. The corresponding probability density of diffusivities is composed of a mixture of delta functions. FIG. 3f shows a novel model called "DIAMOND," discussed in more detail below, which captures the multidimensional diffusivity and heterogeneity of each compartment using peak-shaped distributions of multidimensional diffusivities. The expectation of each matrix-variate distribution captures the compartment overall diffusivity while the distribution concentration captures its microstructural heterogeneity. Specifically, a distribution with a broad peak indicates a highly heterogeneous compartment.

Some embodiments are directed to using a parametric model to predict a diffusion signal represented in diffusion-weighted data, wherein the parametric model is based on a 3-D generalization of equation (3). In this novel model, ADCs are extended to be diffusion tensors, and each population of 3-D diffusivities (tensors) is described with a matrix-variate Gamma distribution. Unlike previous models, such an approach explicitly models the signal arising from each tissue compartment, and represents a model of the tissues. It enables assessment of the mean, axial and radial diffusivity of each compartment separately (cMD, cAD, cRD) and provides a measure of heterogeneity for each compartment.

Some embodiments are directed to a novel DCI technique that characterizes the distribution of 3-D anisotropic microstructural environments in diffusion-compartment imaging (referred to as "DIAMOND" herein). Measurements arising from a large number of 3-D spin packets are considered such that each homogeneous spin packet undergoes local anisotropic 3-D diffusion represented by a diffusion tensor D. Each voxel may be assumed to contain heterogeneous populations of heterogeneous spin packets, and each population may be described with a mv-Γ distribution of spin packets. The signal at each voxel may be modeled by mathematical integration of the contributions of each 3-D spin packet, which has an analytical solution. In some implementations, for each compartment, a priori information about the expected shape of the spin packets distribution can be introduced to represent free, isotropically restricted, intra-axonal, and hindered diffusion arising from each white matter fascicle in each voxel.

Results obtained using the novel DCI technique described herein have been compared with numerous in-silico and in-vivo experiments and with pathological DW-MRI, as described in more detail below. These comparisons demonstrate that the angular error of DIAMOND favorably compares to other approaches such as the ball-and-stick model, described above. Insight into the model parameters of DIAMOND via various numerical simulations of tissue microstructures, such as varying axonal radius and varying fascicle dispersion, are also discussed below. These simulations show that DIAMOND better predicts the DW signal compared to NODDI, with both simulations and in-vivo data, providing evidence that DIAMOND better captures the underlying DW signal formation. DIAMOND may also provide novel biomarkers reflecting the tissue integrity, as discussed in more detail below.

DIAMOND: an Illustrative Generative Model for Diffusion-Based Imaging

Realizing the limitations of the above-described techniques, some embodiments relate to a novel technique for modeling diffusion-weighted data with a generalized parametric model that more accurately characterizes the tissue microstructures in each voxel. In this novel technique, measurements of the DW signal arising from the large number of spin packets within a voxel are considered. Spin packets travel along different trajectories and are confronted with different barriers to displacement. Three-dimensional spin-packets are considered so that when interacting with an homogeneous portion of the microstructure these spin-packets give rise to anisotropic 3-D Gaussian diffusion represented by a diffusion tensor D, whose contribution to the signal for a diffusion gradient $g_k$ is: $S_0 \exp(-b_k g_k^T D g_k)dD$. This enables the ability to capture the local 3-D structure of the restriction and hindrance to diffusion of water molecules. The fraction of spin packets described by a 3-D diffusivity D in the voxel is given by a matrix-variate distribution P(D) and the DW signal $S_k$ is modeled by:

$$S_k = S_0 \int_{D \in Sym^+(3)} P(D)\exp(-b_k g_k^T D g_k)dD, \qquad (4)$$

where $Sym^+(3)$ is the set of 3×3 SPD matrices.

If a voxel consisted of exactly one homogeneous microstructural environment characterized by a tensor $D^0$, P(D) would be a delta function $P(D)=\delta(D-D^0)$ and the DIAMOND model would be equivalent to DTI. If it consisted of several identifiable homogeneous microstructural environments, a mixture of delta functions would be used, as shown in FIG. 3e. More realistically, each microstructural environment contains some degree of heterogeneity, and is more appropriately described by a population of spin packets. This can be accounted for by modeling the composition of each microstructural environment with a peak-shaped matrix-variate distribution of spin packets centered around $D^0$ and defined over the space of SPD matrices, as shown in FIG. 3f.

Figure 4:
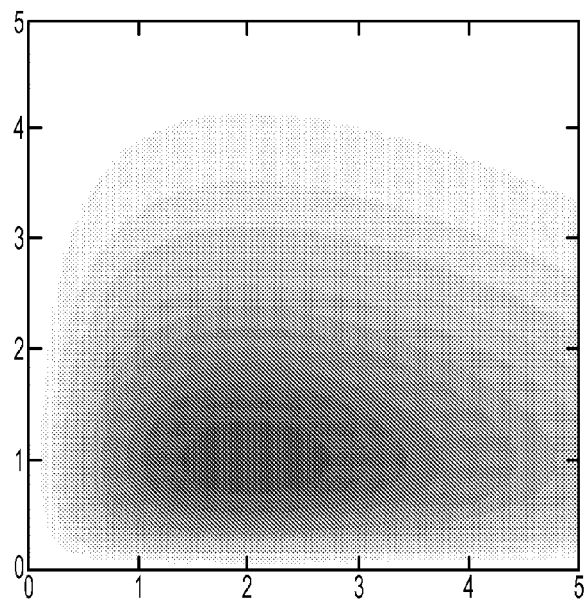
FIG. 4 illustrates a cross-section of the density for symmetric positive-definite (SPD) matrices whose off-diagonal entries are equal to zero.

A natural peak-shaped distribution for SPD matrices is the matrix-variate Gamma (mv-Γ) distribution shown in FIG. 4. FIG. 4 illustrates the density (3) on $Sym_2^+$ with concentration parameter κ=3 and mean parameter $D^0=1.5\text{Diag}(2, 1)$, so that the mode of the density is at $M^0=\text{Diag}(2, 1)$. Shown is a cross-section of the density for SPD matrices D whose off-diagonal entries are equal to zero. The horizontal and vertical axes are the first and second diagonal entries of D, respectively.

A p×p SPD random matrix $D \in Sym^+(p)$ follows a mv-$\Gamma$ distribution with shape parameter $\kappa > (p-1)/2$ and scale parameter $\Sigma \in Sym^+(p)$ if it has density:

$$P_{\kappa,\Sigma}(D) = \frac{|D|^{\kappa-(p+1)/2}}{|\Sigma|^\kappa \Gamma_p(\kappa)} \exp(-\text{trace}(\Sigma^{-1}D)), \quad (5)$$

where $|\cdot|$ is the matrix determinant and $\Gamma_p$ is the multivariate gamma function:

$$\Gamma_p(\kappa) = \pi^{p(p-1)/4} \prod_{j=1}^{p} \Gamma[\kappa - (j-1)/2]. \quad (6)$$

The expectation of $\Gamma_p$ is $D^0 = \kappa\Sigma$, and its mode is $M^0 = D^0(\kappa-1)/\kappa$. The shape parameter $\kappa$ determines the concentration: for constant $D^0$, the density becomes more concentrated around $D^0$ as $\kappa$ increases. The presence of $N_p$ populations of spin packets in slow exchange in a voxel may be considered and the composition of each population may be represented with a mv-$\Gamma$ distribution of spin packets $P_{\kappa_j,\Sigma_j}(D)$ with parameters $\kappa_j$ and $\Sigma_j$, $j \in [1, \ldots, N_p]$. This amounts to the mixture:

$$P(D) = \sum_{j=1}^{N_p} f_j P_{\kappa_j,\Sigma_j}(D), \quad (7)$$

where $f_j \in [0,1]$ are the fractions of occupancy and sum to one. Combining equations (4) and (7) yields:

$$S_k = S_0 \sum_{j=1}^{N_p} f_j \int_{D \in Sym+(3)} P_{\kappa_j,\Sigma_j}(D) \exp(-b_k g_k^T D g_k) dD, \quad (8)$$

The integrals on the right-hand side of equation (8) are Laplace transforms of $P_{\kappa_j,\Sigma_j}(D)$, which have a known analytical expression. This leads to the following model of the DW signal for a gradient direction $g_k$:

$$S_k = S_0 \sum_{j=1}^{N_p} f_j \left(1 + \frac{b_k g_k^T D_j^0 g_k}{\kappa_j}\right)^{-\kappa_j} = \quad (9)$$

$$S_0 \sum_{j=1}^{N_p} f_j \exp\left(-\kappa_j \log\left(1 + \frac{b_k g_k^T D_j^0 g_k}{\kappa_j}\right)\right) = S_0 \sum_{j=1}^{N_p} f_j \mathcal{D}(D_j^0, \kappa_j),$$

where $D_j^0 = \kappa_j \Sigma_j$ is the expectation of the $j^{th}$ mv-$\Gamma$ distribution.

$$\mathcal{D}(D^0, \kappa) = S_0 \left(1 + \frac{b_k g_k^T D^0 g_k}{\kappa}\right)^{-\kappa}$$

denotes the non-monoexponential decaying signal arising from a population of spin packets described by $P_{\kappa,\Sigma}(d^0 = \kappa\Sigma)$. Finite values of $\kappa_j$ capture the heterogeneity of each population of spin packets as shown in FIG. 3f. Specifically, a distribution with a sharp peak indicates a population with a highly homogeneous microstructure, and a distribution with a broad peak indicates a highly heterogeneous population.

Equation (9) provides a generalized expression of the DW signal arising from heterogeneous populations (e.g., different fascicles) of heterogeneous spin packets in each voxel. Prior knowledge of the presence of specific microstructural environments in voxels may be introduced. For example, some voxels likely contain water molecules that undergo free diffusion at the measured diffusion scale due to partial volume effect with CSF. This can be modeled with a mv-$\Gamma$ distribution $P_{\kappa_{free},\Sigma_{free}}$ with isotropic mode $M_{free}^0 = \text{diag}(3 \times 10^{-3})mm^2/s$ with shape parameter $\kappa_{free}$ and volumic fraction $f_{free}$. Cytotoxic brain edemas which occur in ischemic strokes and in traumatic brain injuries are characterized by intracellular water accumulation caused by an increased cell membrane permeability for ions and by ionic pump failure due to energy depletion. This leads to a greater proportion of water molecules inside glial cells, where diffusion is macroscopically isotropic but becomes restricted. This isotropic restricted diffusion may be captured by considering a second distribution with isotropic mode $M_{iso,r}^0$, shape parameter $\kappa_{iso,r}$ and volumic fraction $f_{iso,r}$. The diffusion of water molecules restricted and hindered by a fascicle j may both be represented by a single mv-$\Gamma$ distribution with anisotropic cylindrical $M_j^0$, shape parameter $\kappa_j$ and volumic fraction $f_j$ leading to the signal generation model:

$$S_k f_{free} \mathcal{D}(D_{free}^0, \kappa_{free}) + f_{iso,r} \mathcal{D}(D_{iso,r}^0, \kappa_{iso,r}) + \sum_{j=1}^{N_f} f_j \mathcal{D}(D_j^0, \kappa_j), \quad (10)$$

where $N_f = N_p - 2$ is the number of fascicles in the voxel. This model has $6N_f + 4$ free parameters. Alternatively, the diffusion of water molecules restricted to the intra-axonal space of a fascicle j and the surrounding hindered extra-axonal molecules may each be represented by a mv-$\Gamma$ distribution with anisotropic cylindrical $M_{j,r}^0$ (intra-axonal restricted) and $M_{j,hin}^0$ (hindered) with identical eigenvectors and with shape parameters ($\kappa_{j,r}, \kappa_{j,hin}$) and volumic fractions ($f_{j,r}, f_{j,hin}$):

$$S_k f_{free} \mathcal{D}(D_{free}^0, \kappa_{free}) + f_{iso,r} \mathcal{D}(D_{iso,r}^0, \kappa_{iso,r}) + \quad (11)$$

$$\sum_{j=1}^{N_f} [f_{j,r} \mathcal{D}(D_{j,r}^0, \kappa_{j,r}) + f_{j,hin} \mathcal{D}(D_{j,hin}^0, \kappa_{j,hin})],$$

In some embodiments, a tortuosity model may be employed to constrain the diffusivities of water molecules inside and around axons resulting in only two additional free parameters per fascicle compared to equation (10): the intra-axonal volume fraction $$v_j = \frac{f_{j,r}}{f_{j,r} + f_{j,hin}}$$

and one additional concentration parameter per fascicle ($\kappa_{j,r}$ and $\kappa_{j,hin}$ instead of $\kappa_j$).

In some embodiments, the parameters of the DIAMOND model at each voxel may be estimated using a maximum a posteriori approach. V denotes the image domain, y denotes the set of $N_g$ DW images and $y_k^i$ denotes the $i^{th}$ voxel of the gradient image k. A variable number $N_{P_i}$ of populations of spin packets for each voxel i is considered.

$$D = (D_1^{0,i}, \ldots, D_{N_{P_i}}^{0,i}, i \in V) \text{ and } \kappa = (\kappa_1^{0,i}, \ldots, \kappa_{N_{P_i}}^{0,i}, i \in V)$$

denote the parameters of the mv-Γ distribution for each population, and $$f = (f_1^i, \ldots, f_{N_{P_i}}^i, i \in V)$$

denotes the corresponding fractions of occupancy. The tensors D are parameterized in the log-domain by setting $$L = (\log(D_1^{0,i}), \ldots, \log(D_{N_{P_i}}^{0,i}), i \in V)$$

to ensure the estimation of positive-definite matrices. The estimation of the model parameters is performed by maximizing:

$$\{\hat{L}_{MAP}, \hat{\kappa}_{MAP}, \hat{f}_{MAP}\} = \underset{L,\kappa,f}{\mathrm{argmax}}\, p(L, \kappa, f \mid y) = \underset{L,\kappa,f}{\mathrm{argmax}}\, p(y \mid L, \kappa, f) p(f \mid \kappa, L) p(\kappa \mid L) p(L). \quad (12)$$

The parameters $\hat{D}_{MAP}$ may be computed as $\exp(\hat{L}_{MAP})$. In this embodiment, prior knowledge about the estimated fractions and shape parameters κ is not considered so that $p(f|\kappa,L)$ and $p(\kappa|L)$ are uniform densities. In other embodiments, prior knowledge about the estimated fractions and shape parameters κ may be considered. In this embodiment, the noise was assumed to be Gaussian (zero-mean and variance $\sigma^2$) and independent between images and between voxels, so that:

$$p(y \mid L, \kappa, f) = \prod_{i \in V} \frac{1}{\sigma\sqrt{2\pi}} \exp\left(-\frac{\sum_{k=1}^{N_g} \|S_k(\exp(L^i), \kappa^i, f^i) - y_k^i\|^2}{2\sigma^2}\right), \quad (13)$$

where $S_k$ is given by equation (9). A regularization prior $p(D)$ that exploits spatial homogeneity is considered by setting $p(L) \propto \prod_{i \in V} \prod_{j=1}^{N_p} \exp(-\alpha_{reg} \phi(\|\nabla L^{i,j}\|))$, where $\|\nabla L^{i,j}\|$ is the norm of the spatial gradient of $L^{i,j}$, $\alpha_{reg}$ is a parameter controlling the regularization strength, and $\phi(s) = \sqrt{1 + s^2/K_{reg}^2}$ accounts for anisotropic regularization and preserves sharp contours. In some embodiments, $\|\nabla L^{i,j}\|$ may be approximated by finite difference after identifying the log-tensor most similar to $L^{i,j}$ in each neighboring voxel.

Although a Gaussian distribution of the noise is assumed in this embodiment, it should be appreciated that in other embodiments, the noise may be assumed to have a non-Gaussian distribution. For example, in some embodiments, the noise may be assumed to have a distribution that is Rician or non-central Chi-squared.

Parametric models for use with embodiments of the invention may be implemented in any suitable way including any suitable combination of hardware and software, and aspects of the invention are not limited in this respect. In some embodiments, the DIAMOND estimation algorithm is implemented in C++ and parallelized over the image space. In some embodiments, numerical optimization (equation (12)) may be achieved with the BOBYQA algorithm described by Powell (*The BOBYQA algorithm for bound constrained optimization without derivatives. In Technical report NA2009/06. Department of Applied Mathematics and Theoretical Physics*, Cambridge, England), a derivative-free bound-constrained optimization technique. BOBYQA is an iterative algorithm. At each iteration, it computes from a set of points a quadratic approximation for the objective function. The point giving the largest value for the objective function is replaced by the minimum of the quadratic approximation computed in a trust region. At each iteration the trust region is updated. BOBYQA converges faster than the Newton method and is less sensitive to local minima compared to gradient descent algorithms such as conjugate gradient or Levenberg-Marquardt. The orientation of the $L_i$'s was parameterized with the Euler angles, as they empirically led to a more efficient optimization. Tensors and fractions were initialized and concentration parameters κ's were initialized to 100 (high compartment homogeneity). Optimization was achieved by gradually increasing the model complexity, from a single stick model to the ball-and-stick to the estimation of the full DIAMOND model. The spatial regularization was achieved by iteratively refining the model parameters over the image while progressively increasing the regularization parameter $\alpha_{reg}$ in [0, 1], with $K_{reg}=0.01$.

As described in more detail below, when comparing the performance of the DIAMOND model against other models, the number of fascicles $N_f$ was estimated at each voxel i by first considering $N_{f_i}=0$ and by increasing $N_{f_i}$ (up to three) as long as it significantly decreases the generalization error. The DIAMOND model described by equation (10) with $f_{iso,r}=0$ was considered, leading to $6N_{f_i}+2$ free parameters per voxel. The total running time for a typical DWI acquisition with matrix size 128×128 was approximately seven minutes per slice with a Pentium Xeon E5-2687 W processor with eight cores.

As discussed above, novel parametric models designed for use with some embodiments are configured to be fitted to a set of DWI data having multiple non-zero b-values. Any suitable technique may be used to generate DWI data having multiple non-zero b-values, and embodiments are not limited in this respect. In some embodiments, the Cube and Sphere (CUSP) gradient encoding scheme, described in more detail below may be used to generate the set of DWI data.

CUSP combines spherical and cubic sampling in q-space, achieving a large number of non-zero b-values with short TE, high SNR and high angular coverage. Briefly, CUSP is based on a modification of a 2-shell HARDI. In contrast to a multi-shell HARDI, the pulse duration and separation δ and Δ of the PGSE sequence are fixed to achieve the b-value of the inner shell (instead of the outer-shell for multi-shell HARDI), which requires a shorter TE and provides a significant SNR boost. The gradients of the outer shell have maximally separated gradients orientation with respect to the inner shell but cannot be imaged with the fixed low δ and Δ. Instead, their strength is reduced so that they lie in the cube enclosing the inner shell. This cube is a cube of constant TE in q-space, in which any gradient can be imaged without modification of δ and Δ but by appropriate application of the gradient system. This enables imaging b-values up to three time the b-value of the inner-shell, corresponding to the diffusion gradients g=(±1±1; ±1). CUSP enables imaging of multiple b-value with low TE, high SNR and high angular coverage.

In some embodiments, a CUSP65 encoding scheme which includes 5 b=0 s/mm² images, 30 gradients on the inner shell at b=1000 s=mm² and 30 gradients on the cube of constant TE providing gradients with b-values between 1000 s=mm² and 3000 s=mm² is used. However, it should be appreciated that any other suitable gradient encoding scheme may alternatively be used to generate a set of diffusion-weighted images having multiple non-zero b-values.

As discussed above, some embodiments are directed to application of a novel diffusion model to diffusion-weighted data having multiple non-zero b-values. The model is motivated by biophysical considerations of the microstructure giving rise to the DW signal and that can be applied in clinical practice. Measurements of the signal arising from 3-D spin packets within each voxel were considered and each population of 3-D spin packets was characterized by estimation of a peak-shaped statistical distribution of diffusion tensors, as described above in connection with FIG. 3f.

The peak-shaped matrix-variate Gamma distribution $P_{\kappa,\Sigma}$ was considered, which enables computation of an analytical solution to equation (4). The matrix-variate Gamma distribution generalizes the Wishart distribution by allowing a non-integer number of degrees of freedom. Previously, others investigated a spherical deconvolution approach in which the basis functions were Wishart distributions with fixed diffusivity, fixed number of degrees of freedom (m=4) and fixed orientations distributed over the unit sphere. The number of Wishart components (N>100) was linked to the discretization resolution of the fascicle orientation distribution function (fODF), irrespective of the number of underlying tissue compartments present in each voxel. Importantly, this corresponds to a model of the signal. It focuses on estimating a distribution of orientations at a single non-zero b-value without assumption about the underlying tissue microstructure, and does not provide insight into the tissue compartments giving rise to the signal. Recent works have investigated subsequent extraction of tissue information from the shape of the fODF such as the apparent fiber density (AFD). However, because the fODF is defined at a single b-value, the information about various diffusion scales is missed and the provided tissue information is limited. In addition, and similarly to NODDI, spherical deconvolution approaches rely on the fundamental hypothesis that a single prefixed fascicle response function (FRF) can well model the entire brain white matter. This is inconsistent with the known presence of many axonal diameters and many degrees of myelination throughout the brain, and the interpretation of extracted tissue parameters from the fODF remains unclear. While extracting a FRF in each voxel was investigated recently, only a single FRF can be employed to deconvolve the signal in a voxel and the signal arising from two crossing fascicles with different characteristics (e.g., healthy and not healthy) cannot be modeled.

In contrast, DIAMOND focuses on capturing the distributions of 3-D diffusivities arising from each tissue compartment (see FIG. 3) and corresponds to a model of the tissues. It requires the estimation of the number of tissue compartments, i.e., the number of mv-Γ components. This was achieved by assessing the generalization error of models of increasing complexity in each voxel. Unlike previous models, DIAMOND requires the acquisition of multiple non-zero b-values to disentangle the decay curves arising from each tissue compartment and provides information at various diffusion scales. Importantly, estimating a distribution of diffusivities requires that all b-values are acquired with the same mixing times δ and Δ, ruling out the use of multiple separate single shells with optimized TE as employed in the WU-Minn Human Connectome Project. As discussed above, in some embodiments, the diffusion data is acquired using the CUSP gradient scheme, which images a large number of different b-values with uniform angular coverage and low TE, providing a substantial SNR boost compared to a multi-shell HARDI acquisition.

The parameters of DIAMOND provide a macroscopic description of the tissue microstructure in each compartment. The expectation $E[P_{\kappa,\Sigma}]=D^0=\kappa\Sigma$ of each distribution $P_{\kappa,\Sigma}$ is a tensor that describes the average 3-D diffusivity from which the axial and radial diffusivity of each compartment (cAD and cRD) can be derived. The concentration parameter κ of $P_{\kappa,\Sigma}$ captures the overall compartment's heterogeneity.

More precisely, a mv-Γ component with a small κ (broad peak) describes the presence of heterogeneous 3-D diffusivities in the compartment, suggesting a heterogeneous microstructure. In contrast, a mv-Γ component with a large κ (sharp peak) indicates an homogeneous microstructure. Importantly, κ captures any heterogeneity that is consistent with an (oriented) 3-D compartment. Such heterogeneity may result from heterogeneity in fascicle orientation, in axonal diameter, in axonal density, or from undulation of axons.

Modeling together multiple sources of heterogeneity is not a limitation. There are many possible sources of heterogeneity at different diffusion scales, and it is not clear whether they can be captured separately when using a clinical scanner with long δ and δ≈Δ and clinically compatible scan times. The NODDI approach suggested that the fascicle dispersion and the intra-volume cellular fraction (ICVF) could be specifically assessed by relying on a fixed representation of a WM fascicle throughout the brain. The simulations described herein illustrate that, when the simulated microstructure differs from the prefixed fascicle microstructure, the diffusion profile estimated by NODDI substantially deviates from the true profile, even without noise.

As discussed more detail below, the experiments discussed herein demonstrate that when the fascicle's diffusivity is fixed, variations of the signal due to a varying microstructure are captured by the only remaining free parameters, and changes in those parameters are not consistent with the simulated microstructure. Particularly, it was found that variation of the axonal radius was captured by variations of the ICVF with NODDI, while a constant ICVF was simulated, as discussed below in connection with FIG. 7A. Instead, DIAMOND estimates for each tissue compartment its fraction of occupancy, its average 3-D diffusivity, and a measure that quantifies the overall microstructural heterogeneity. The simulations described herein show that axonal dispersion is captured by an increased heterogeneity of 3D diffusivities and a decreased cAD, as expected. Also shown below is that the cRD increases with increasing axonal radii. Using in-vivo data, it was demonstrated that accounting for each compartment heterogeneity substantially reduces the error in predicting the signal, as discussed in connection with FIG. 8 below, indicating that DIAMOND better captures the biophysical mechanisms underlying the DW signal formation compared to other diffusion models.

In contrast to DTI and NODDI, the techniques described herein consider the presence of multiple fascicles per voxel, e.g., the presence of multiple anisotropic compartments. The evaluation of the DIAMOND model described herein shows that the estimated number of fascicles and the estimated fascicle orientations match the known anatomy, both with high-resolution and high-SNR DWI and with an acquisition with a moderate number of DW images achievable in clinical practice. In contrast to CHARMED, the results of the DIAMOND model indicate that the fascicle orientations can be estimated with b-values b≤3000 s/mm². Importantly, estimation of the concentration parameter κ of the matrix-variate Gamma distribution may provide an important marker of abnormal tissue. As discussed further below in connection with FIG. 10C, this parameter was different between normal and abnormal tissue in TSC, and an increased heterogeneity along the fascicle located in a tuber in a TSC patient was observed. These observations may reflect heterogeneous myelination or heterogeneous mixture of glial cells as observed in mice models of TSC.

In contrast, no significant heterogeneity consistent with unrestricted diffusion was observed. DIAMOND also provides the fraction of unrestricted water diffusion. As discussed further below, increased unrestricted diffusion was observed in the region of the tuber, which might reflect an increased extra-cellular space, the presence of perivascular spaces, or the presence of giant cells typically observed in TSC brain specimens.

Experiment 1: Assessment of Angular Detection Accuracy

Figure 5:
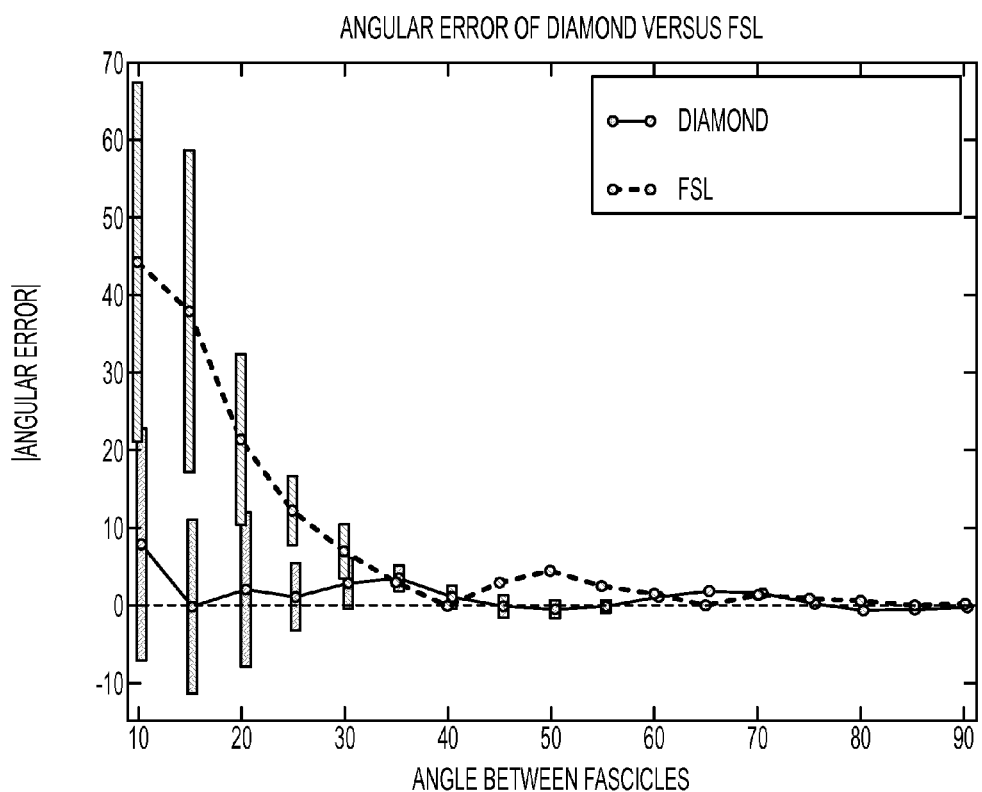
FIG. 5 shows a plot of angular detection accuracy for a ball-and-stick model and a novel DIAMOND model used in accordance with some embodiments.

Fascicles crossing at varying angles (0 to 90°) were simulated and the angular reconstruction error of DIAMOND was compared with the ball-and-stick model as implemented in FSL. For each crossing angle, the DW signal arising from the multi-tensor model was simulated as:

$$S_k = S_0[f_{free} \exp(-b_k D_{free}) + f_1 \exp(-b_k g_k^T D_1 g_k) + f_2 \exp(-b_k g_k^T D_2 g_k)], \quad (14)$$

with $D_{free}=3\times10^{-3}$ mm²/s; $f_{free}=0.15$; $f_1=0.60$; $f_2=0.25$; Trace($D_1$)=Trace($D_2$)=$2.1\times10^{-3}$ mm²/s; FA($D_1$)=FA($D_2$)=0.9; CUSP65 encoding scheme; Rician-noise corruption with SNR=30 dB. The simulations were repeated 1000 times and the DIAMOND and the ball-and-stick models were estimated for each of them. The average and standard deviation of the angular error between the estimated fascicle orientations were compared, as shown in FIG. 5. As shown, the angular accuracy of DIAMOND favorably compares to that of the ball-and-stick model, particularly for small angles.

Experiment 2: Assessment of Modeled Diffusion Profile and Interpretability of Model Parameters The ability of DIAMOND and NODDI to capture the diffusion profile was compared by generating realistic synthetic diffusion data with Monte-Carlo simulations using the Camino toolkit (200000 walkers, 5000 time points). Two axonal geometries were considered: 1) aligned cylinders of varying radii (1 μm to 10 μm) and 2) cylinders crossing at 45°. The signal was simulated for 100 voxels with CUSP65 and with parameters typically achievable with a clinical scanner: pulse duration δ=30 ms, pulse separation Δ=40 ms, TE=90 ms, maximum gradient strength of G=0.040 T/m and Rician noise corruption (SNR=30 dB on the b=0 s/mm² image). NODDI parameters were estimated using the publicly available NODDI toolbox (http://cmic.cs.ucl.ac.uk/mig/). The estimated diffusion profiles of DIAMOND and NODDI were plotted and compared (mean error and standard deviation over the 100 voxels). Variations of DIAMOND's and NODDI's model parameters for increasing axonal radii were investigated.

Voxels with various axonal orientation dispersion were also simulated. In each voxel 10000 cylinders were simulated with orientations drawn from a Watson distribution with increasing dispersion indices. The signal was simulated with the CUSP65 scheme (δ=30 ms; Δ=40 ms; TE=90 ms; $G_{max}$=0.040 T/m) by using the analytical expression of the diffusion in sticks.

FIG. 6 shows the diffusion profiles of DIAMOND and NODDI computed from the Monte-Carlo simulations. The parameters of each diffusion model were estimated using the CUSP65 gradient encoding scheme. The plots report the average signal modeled by DIAMOND and NODDI for gradients distributed in the x-z plane obtained by a rotation around the y axis, for b=1000 s/mm² and b=2000 s/mm². The average was computed over 100 repetitions of the simulations. The standard deviation over the 100 repetitions is reported as the shaded portion surrounding the lines. The dashed line shows the ground truth.

Figure 6E:
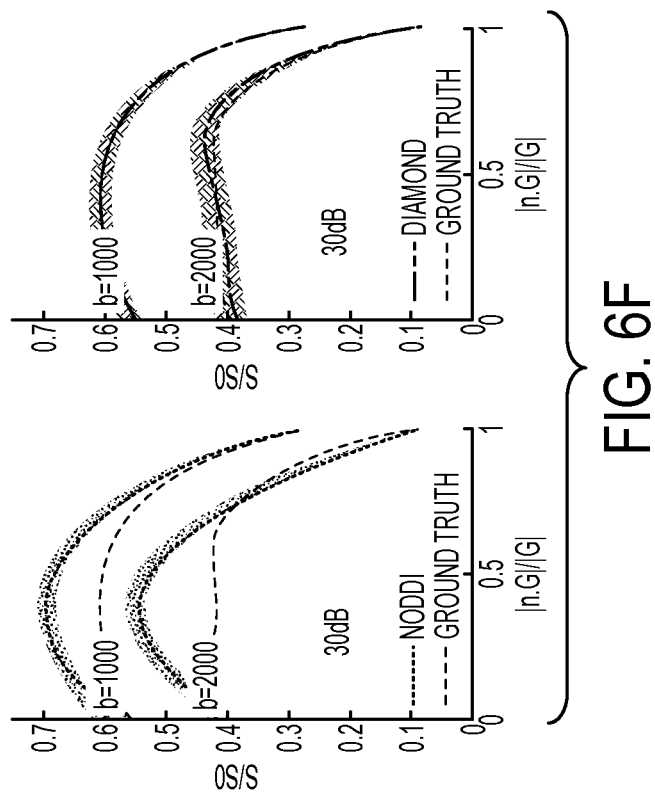
FIG. 6 shows simulation results comparing the NODDI model and a novel DIAMOND model used in accordance with some embodiments.
Figure 6F:
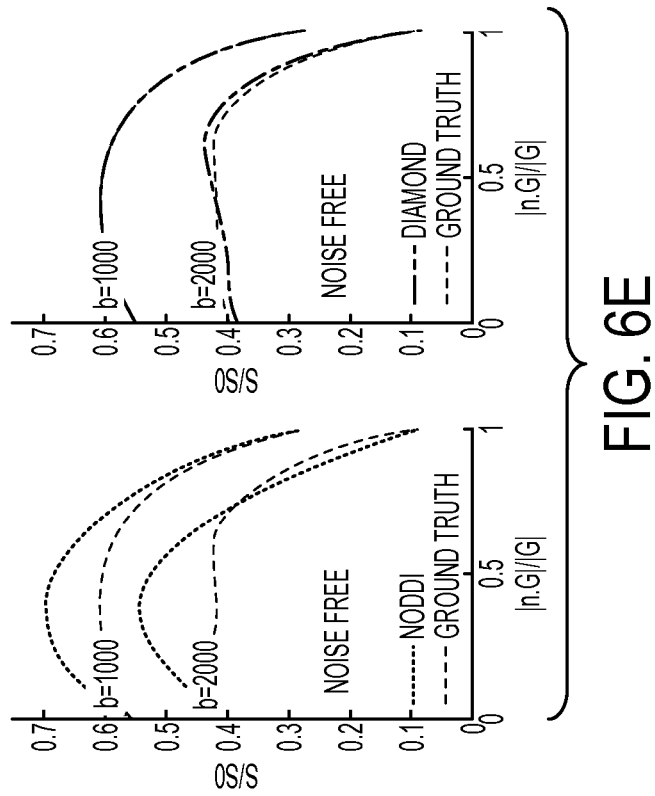
Figure 8A:
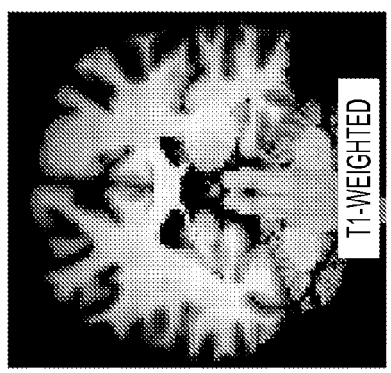
FIG. 8 shows a comparison of different diffusion models with in-vivo data by assessing their generalization error.
Figure 8B:
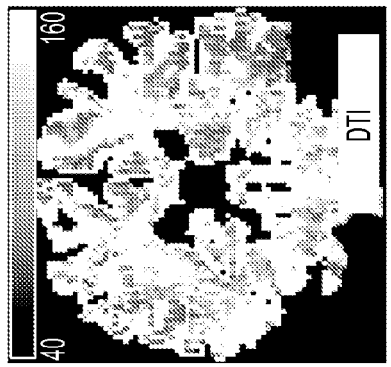
Figure 8C:
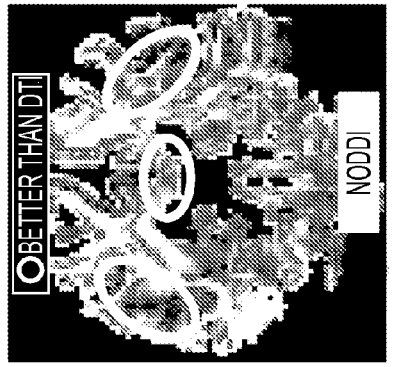
Figure 8D:
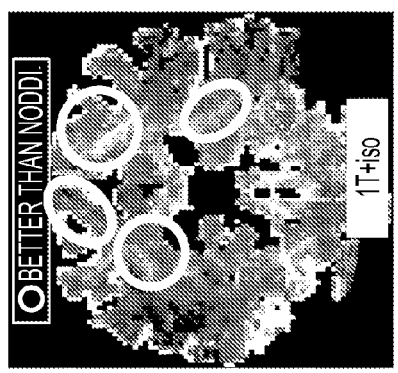
Figure 8E:
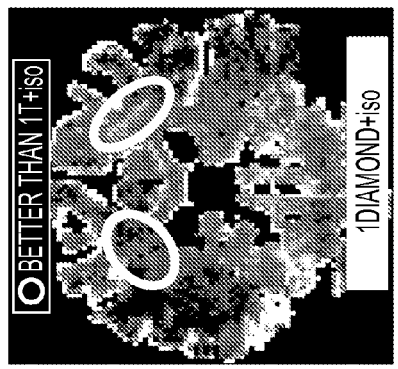
Figure 8F:
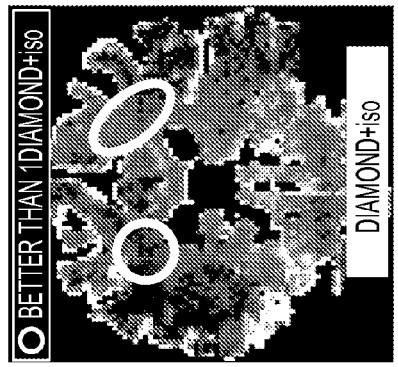

FIGS. 6A and 6B illustrate results for simulations with cylinders of radius 1 μm oriented along the z-axis. FIGS. 6C and 6D illustrate results for simulations with cylinders of radius 10 μm oriented along the z-axis. FIGS. 6C and 6D show that when the simulated microstructure differs from NODDI's prefixed fascicle response function, NODDI's resulting diffusion profile significantly deviates from the ground truth, even in the noise-free case, as shown in FIG. 6C. In contrast, the diffusion profile of DIAMOND is substantially closer to the ground truth for both the R=1 μm (FIGS. 6A, 6B) and R=10 μm (FIGS. 6C, 6D) axonal radii for both the noise-free (FIGS. 6A, 6C) and noisy data (FIGS. 6B, 6D). FIGS. 6E and 6F illustrate results for simulations with crossing cylinders. The simulation results in FIGS. 6A, 6C, and 6E are based on an infinite SNR, and the simulation results in FIGS. 6B, 6D, and 6F are based on an SNR=30 dB. FIGS. 6E and 6F show the substantial error of NODDI in voxels with crossing fascicles. This is an important limitation since crossing fascicles occur in 60% to 90% of the voxels in the human brain. In contrast, the diffusion profile is better captured with DIAMOND.

FIG. 7 illustrates variations of DIAMOND and NODDI parameters for various microstructures. FIG. 7A shows the results of simulations for various axonal radii and fixed intra-cellular volume fraction (ICVF=0.7). As shown, with NODDI, variations of the axonal radii are captured by variations of the intracellular volume fraction (ICVF), although a constant ICVF was simulated in CAMINO. In contrast, with DIAMOND, changes in axonal radii are reflected in the compartment's cRD while other parameters (heterogeneity and cAD) remain approximately constant. These changes in cRD are consistent with the known physical behavior of water molecules diffusing more freely in larger axons.

FIG. 7B shows the results of simulations for various fascicle dispersion indexes and fixed ICVF=0.7. For NODDI, the dispersion index (ODI) and the intra-cellular volume fraction (ICVF) parameters are reported. The variability of the curves show the high sensitivity of the underlying optimizer to local minima. Increasing axonal radius is characterized by a decreasing ICVF, as shown in FIG. 7A, while a fixed ICVF was simulated. Increasing dispersion is correctly characterized by an increasing ODI index, as shown in FIG. 7B. For DIAMOND, the axial diffusivity and radial diffusivity of the fascicle compartment (cAD/cRD) are shown and a heterogeneity index (HEI) based on the same transform than the ODI measure: HEI($\kappa$)=$2/\pi$ arctan $(1/\kappa)$ (small values=low heterogeneity; large values=high heterogeneity) is plotted along the vertical axis. The results show that increasing axonal radius is characterized by increasing cRD with constant cAD as shown in FIG. 7A, while increasing axonal dispersion is characterized by decreasing cAD and constant cRD, as shown in FIG. 7B.

FIG. 7B shows that NODDI correctly captures the increased axonal dispersion via the ODI parameter, while a slight decrease in ICVF is observed. DIAMOND captures the increased axonal dispersion as an increased heterogeneity of 3D diffusivities (HEI), which is an expected behavior. Interestingly, the cRD remains constant with increasing dispersion while the cAD decreases. This is consistent with the known physical behavior of water molecules whose diffusion endures more restrictions along the average fascicle orientation when the dispersion increases.

The performance of DIAMOND was compared to various diffusion models with in-vivo acquisitions by assessing their generalization error (GE), which quantifies the capability of each model to accurately predict the DW signal for unobserved gradient directions and strengths, and therefore reflects how well each model captures the mechanisms underlying the signal generation. Acquisitions were carried out using a Siemens 3T Trio scanner with a 32 channel head coil and a pulsed-gradient spin echo (PGSE) DWI sequence with echo-planar imaging (EPI) readout. Eddy current distortion was minimized by utilizing a twice-refocused spin echo sequence. A CUSP90 scheme was used. The CUSP90 scheme augments CUSP65 with 3 inner-shells of 6 directions at b=400; 600; 800 s/mm² and 7 b=0 s/mm² images in order to assess the signal prediction with a wider range of b-values. A healthy volunteer was scanned using two repetitions of CUSP90 providing a total of 180 DW images with the following imaging parameters: FOV=220 mm; matrix=128×128; 71 slices; resolution=1:7×1:7×2 mm³; TR=10704 ms; TE=78 ms. The DW images were corrected for potential head motion during the scan by rigid registration of the DW-images to the b=0 s/mm² image. The gradient orientations were compensated for the rotation component of the transformation for each image. Five tissue models were considered: 1) the single tensor model, 2) NODDI, 3) a multi-tensor model with one isotropic and one anisotropic tensor ($M_{free}^0$=3×10⁻³ mm²/s) (1T+iso), 4) a DIAMOND model with one isotropic and a single anisotropic compartment (1DIAMOND+iso), and 5) the complete DIAMOND model (DIAMOND+iso).

Experiment 3: Model Comparison with In-Vivo Data

FIG. 8 shows a comparison of five diffusion models with in-vivo data by assessment of their generalization error. FIG. 8A illustrates a T1-weighted image of the diffusion signal. FIG. 8B shows the results when DTI is used to predict the diffusion signal shown in FIG. 8A. As shown, DTI is a poor predicator of the diffusion signal, likely because DTI does not account for the non-monoexponential decay and assumes a single compartment per voxel. FIG. 8C shows the results when NODDI is used to predict the diffusion signal. A shown, NODDI provides a lower generalization error than DTI in regions of crossing and close to the cortex because it models the fascicle dispersion and accounts for freely diffusing water. FIG. 8D shows the results when the 1T+iso model is used to predict the diffusion signal. As shown, estimation of all the parameters of the 1T+iso model ultimately enables better prediction of the signal compared to NODDI. FIG. 8E shows the results when the 1DIAMOND+iso model is used to predict the diffusion signal. As shown, accounting for the heterogeneity of 3D diffusivities (DIAMOND) slightly improves the generalization error in regions of crossings. FIG. 8E shows the results when the DIAMOND+iso model is used to predict the diffusion signal. As shown, accounting for each fascicle in each voxel while modeling each compartment heterogeneity provides ultimately the lowest generalization error. Overall, the results show that DIAMOND+iso better predicts diffusion measurements not included in the estimation, supporting the fact that the DIAMOND model better captures the underlying diffusion decay.

Experiment 4: High-Resolution and High-SNR Diffusion Weighted Imaging

DIAMOND reconstruction was achieved from high-resolution and high SNR super-resolved DWI. Three orthogonal anisotropic CUSP65 scans (axial, coronal and sagittal) were acquired with FOV=240 mm, matrix=192×192, and resolution=1:25×1:25×2 mm³; TR=13100 ms and low TE=91 ms. For each orientation, two b=0 s/mm² images were acquired with same parameters as above but opposite phase encoding directions in order to correct the scans for geometric and intensity distortion. The underlying high-resolution isotropic DW images were reconstructed at 1×1×1 mm³ using a quantitative super-resolution technique. The parameters of the DIAMOND model were then estimated at each voxel.

FIG. 9 shows the DIAMOND reconstruction from high-resolution super-resolved DWI. FIG. 9A shows that the estimated number of fascicles at each voxel estimated with the 0.632 bootstrap approach matches the known anatomy. For example, as shown no fascicles were detected in the ventricules (i), a single fascicle was detected in the body of the corpus callosum (ii) and in the corticospinal tracts (iii) and up to three fascicles were detected in the corona radiata (iv). FIGS. 9B-E show fractions of occupancy estimated by DIAMOND for respectively the unrestricted water diffusion and each of the three fascicles. In particular, FIG. 9B illustrates that the amount of cerebrospinal fluid is well captured by the fraction of free water.

Figure 9A:
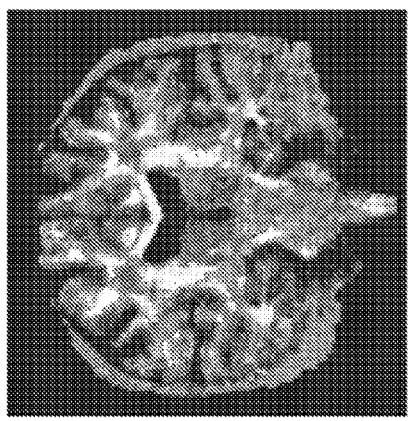
FIG. 9 shows a reconstruction of an image from high-resolution super-resolved DWI data using a novel DIAMOND model in accordance with some embodiments.
Figure 9A:
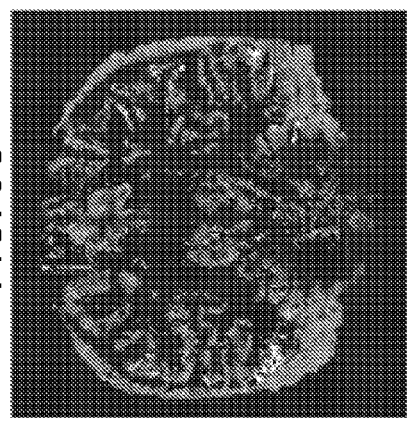
Figure 9A:
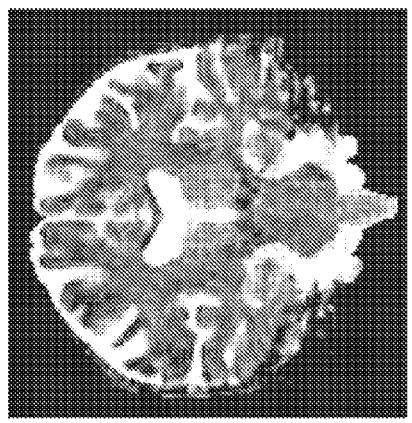
Figure 9A:
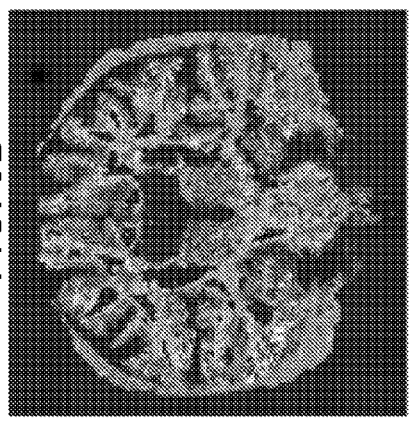
Figure 9A:
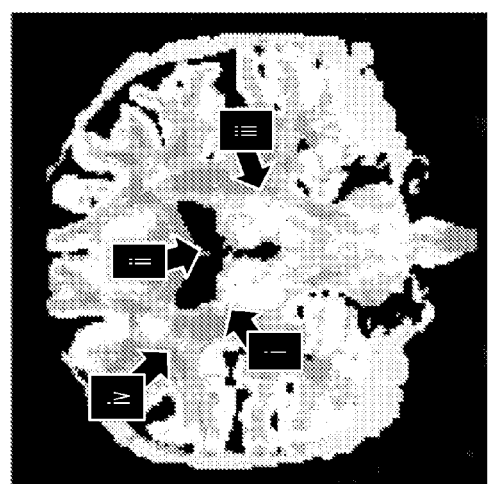
Figure 9F:
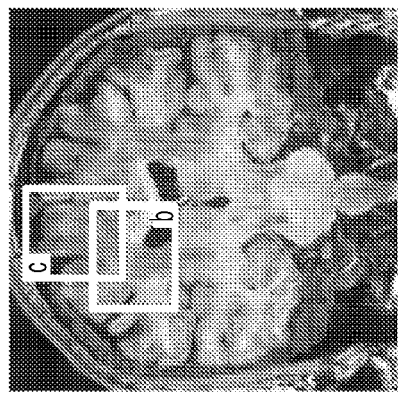
Figure 9G:
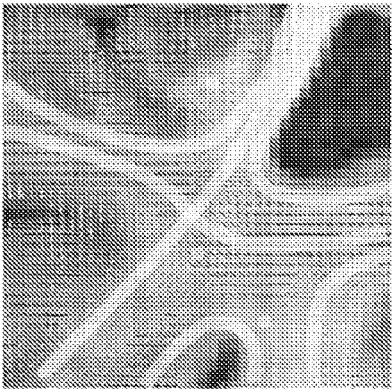
Figure 9H:
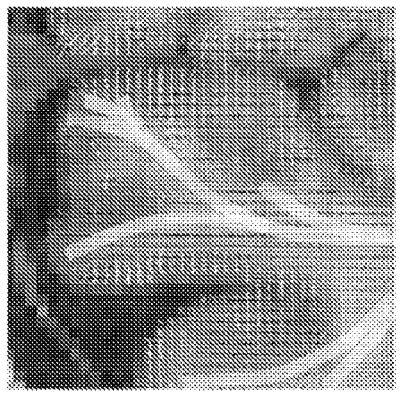

FIGS. 9F-H show the estimated fascicle orientations by DIAMOND. In particular, FIGS. 9F-H report the orientation of the mode of each mv-$\Gamma$ distribution. FIG. 9F shows a coronal slice of the DIAMOND model super-imposed on the T1-weighted image. FIG. 9G shows that DIAMOND correctly captures three crossing fascicles in the corona radiata. FIG. 9H shows that DIAMOND well captures the projection of the fascicles into the grey matter of the cortex.

Figure 9I:
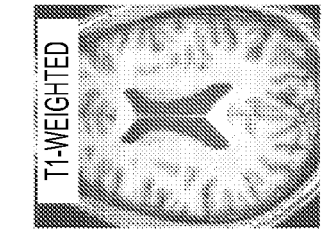
Figure 9J:
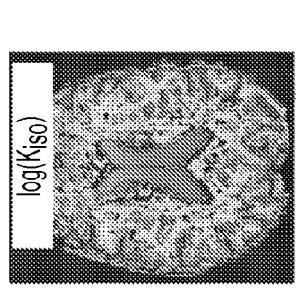
Figure 9K:
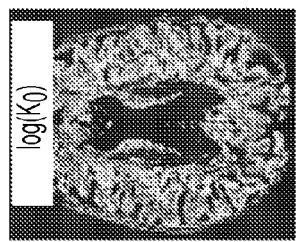
Figure 9L:
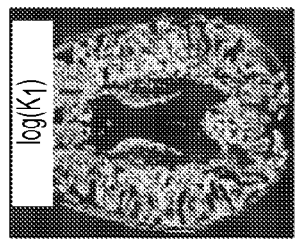
Figure 9M:
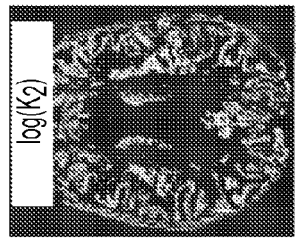

FIGS. 9I-M show the maps of the concentration parameter of the mv-$\Gamma$ distribution describing each compartment, reflecting the intra-compartment homogeneity (ICHO). In particular, FIG. 9I shows an axial slice of the reference T1-weighted image. FIG. 9J shows the logarithm of the concentration parameter for the unrestricted water diffusion compartment. FIGS. 9K-M show the logarithm of the concentration parameter for each of the three fascicles. The logarithm was used in order to enhance the contrast. Larger values of $\kappa \in [1,\infty]$ (white) indicate a sharper peak-shaped distribution, and therefore an increased microstructure homogeneity.

Experiment 5: Assessment of the Distributions of Microstructural Environments in Pathology A patient with Tuberous Sclerosis Complex (TSC), a genetic disorder characterized by the presence of benign tumors throughout the body was imaged. A CUSP65 acquisition scheme (FOV=220 mm, matrix=128×128, resolution=1:7×1:7×2 mm³) was used. The acquisition duration time was less than 12 minutes. Data acquisition was conducted using a protocol approved by the Institutional Review Board (IRB). DIAMOND reconstruction was used and both the estimated fraction of unrestricted water diffusion and the concentration parameter of the matrix-variate Gamma distributions were investigated.

Figure 10C:
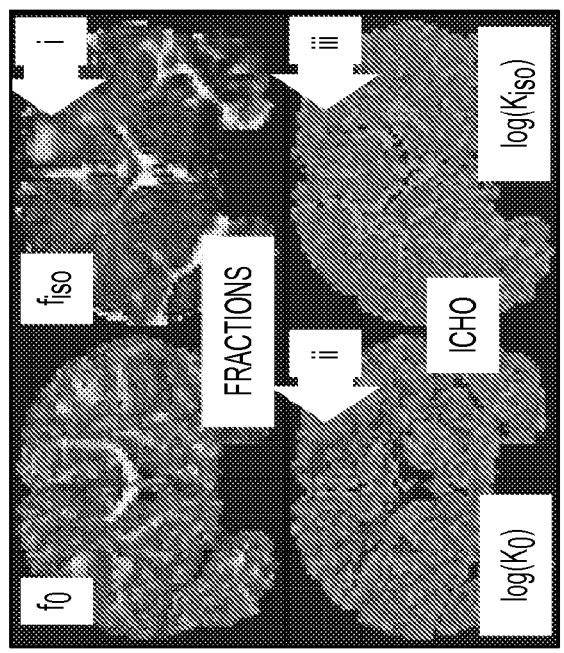
FIG. 10 shows a reconstruction of an image of a patient with Tuberous Sclerosis Complex (TSC) using a novel DIAMOND model in accordance with some embodiments.
Figure 10B:
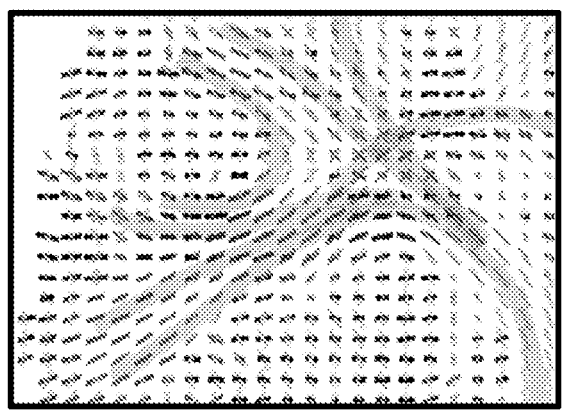
Figure 10A:
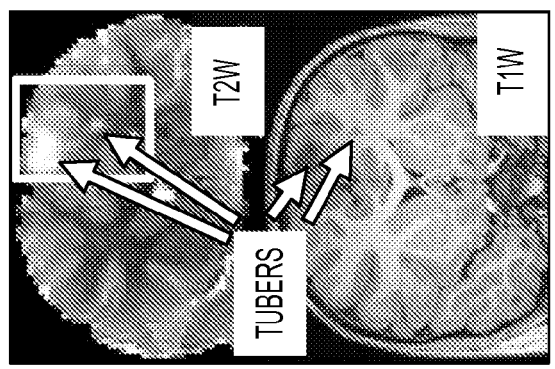

FIG. 10 shows that DIAMOND may provide novel markers of abnormal tissues in disease. Diffusion-weighted data was acquired using the CUSP65 acquisition scheme, described above, and DIAMOND reconstruction was used to model diffusion in the brain of a TSC patient. FIG. 10A illustrates T1-weighted (T1W) and T2-weighted (T2W) images of a TSC brain. The cortical tubers are characterized by an hypo-intensity (dark) on T1W and an hyper-intensity (bright) on T2W. FIG. 10B shows that the estimated fascicle orientations successfully matches the known anatomy, while a single CUSP65 scan with 65 directions was acquired.

FIG. 10C shows the estimated fractions of occupancy (top row) and concentration parameter of the matrix-variate Gamma distributions (bottom row) for the unrestricted diffusion ($f_{iso}$; $\kappa_{iso}$) and for the fascicle of larger fraction of occupancy ($f_0$; $\kappa_0$), indicating that these parameters may provide a novel marker of abnormal tissue. In particular, an increased fraction of unrestricted water diffusion (i) and a decreased intracompartment homogeneity (ICHO) along the fascicle (ii) in the region of the tuber are observed. In contrast, there is no significant change of ICHO for the unrestricted water diffusion compartment (iii).

Figure 11:
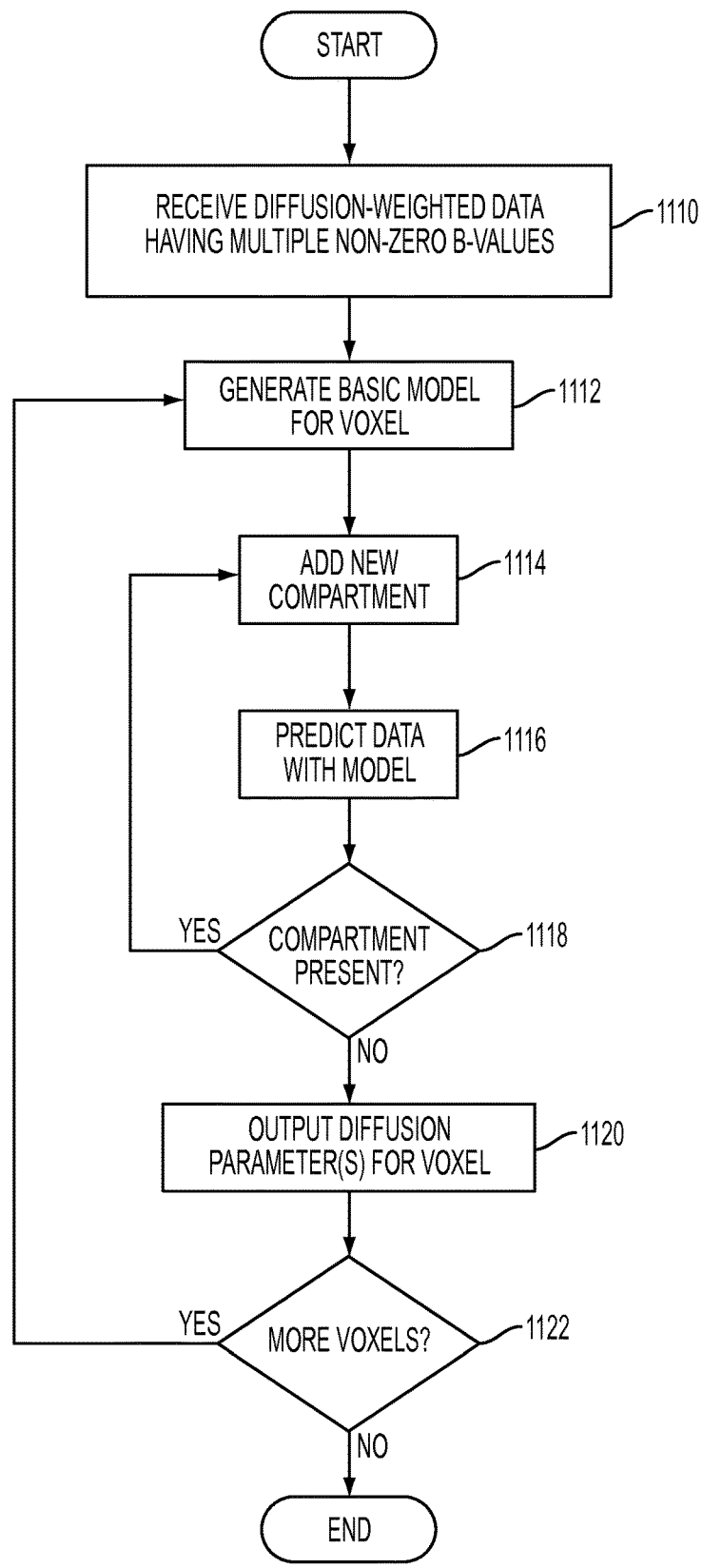
FIG. 11 shows an illustrative process for iteratively fitting a generative model to diffusion-weighted MR data in accordance with some embodiments.

FIG. 11 shows an illustrative process for using a generative parametric model to predict a diffusion signal in accordance with some embodiments. In act 1110, diffusion-weighted data having multiple non-zero b-values is received. As discussed above, the diffusion-weighted data may be acquired using any suitable acquisition technique including, but not limited to the CUSP technique described briefly above, and in more detail below. The process then proceeds to act 1112, where a model for predicting the diffusion signal in a voxel is generated. As described above, in some embodiments a priori information about the tissue microstructure the imaged object in the voxel may be used to generate the model for the voxel, though not all embodiments require the use of such information. In some embodiments, the model generated in act 1112 is based on the DIAMOND model described herein. Alternatively, the model may be any other suitable generative model configured to model multiple tissue compartments, with each compartment being represented by a statistical distribution.

The process then proceeds to act 1114, where a new compartment is added to the model, thereby increasing the model's complexity. The process then proceeds to act 1116, where the diffusion data for the voxel is predicted with the generative model. The process then proceeds to act 1118, where it is determined whether the compartment is present in the voxel. This determination may be made in any suitable way, and embodiments are not limited in this respect. For example, in some embodiments, it may be determined whether there was a statistically significant improvement in the prediction of the model compared to the previous iteration of the model before the compartment was added. When it is determined that a statistically significant improvement in the prediction has been made, it is determined in act 1118 that the compartment is present in the voxel, and the process returns to act 1118, where an additional compartment is added to the model, further increasing the complexity of the model.

The process continues to iterate adding additional complexity to the model until it is determined in act 1118 that the most recently added compartment is not present in the voxel. In some embodiments, the order in which additional compartments are added to the model at each iteration may be predetermined. When it is determined that the newly added compartment is not present in the voxel, the process proceeds to act 1120, where one or more diffusion parameters for the voxel are output. The diffusion parameter(s) may be output in any suitable way, and embodiments are not limited in this respect. For example, in some embodiments, a portion of one or more images based on the diffusion parameter(s) may be created and/or displayed. In other embodiments, information relating to the diffusion parameter(s) may be transmitted to one or more other computers for processing and/or one or more storage devices for storage.

The process then proceeds to act 1122, where it is determined whether there are additional voxels to process. If it is determined that there are additional voxels, the process returns to act 1112, where a new voxel is selected and a model for the newly selected voxel is generated. If it is determined in act 1122 that there are no more voxels, the process ends.

As described above, unlike conventional generative models that make assumptions about the underlying tissue microstructure in a voxel, some embodiments analyze the diffusion signal itself to determine the suitable number of compartments to use in modeling diffusion in the voxel. Due to the generalized nature of the model, this approach relies on the acquired diffusion data to have certain properties that can be used to probe the microstructure of a voxel. One of these requirements is that the diffusion data must be acquired using an acquisition scheme that enables the acquisition of diffusion data having at least two non-zero b-values. An example of such an acquisition scheme is CUSP, as discussed in further detail below.

Acquisition of Diffusion-Weighted Images Having Multiple b-Values: CUSP

Acquiring magnetic resonance images using a longer TE reduces the signal-to-noise ratio for all the measurements, regardless of the applied b-value. Accordingly, acquisitions with a short TE should be favored, particularly when imaging at a high b-value. The minimum achievable TE and nominal b-value follow a complex relationship via the timing parameters δ and Δ, which can be approximated by $$TE \approx \left(\frac{12 b_{nominal}}{\gamma^2}\right)^{1/3}.$$

Consequently, increasing the nominal b-value increases the minimum achievable TE, which in turn leads to an exponentially-decreased signal amplitude closer to the noise floor. Considering that the noise amplitude is constant, this signal dropout leads to a lower SNR for each diffusion-weighted (DW) image, regardless of their b-value. This leads to a fundamental trade-off in diffusion imaging: while higher b-values are known to increase the contrast between the DW gradient directions, and therefore to increase the reliability of estimation of orientation of each fascicle, higher nominal b-values also lead to a longer TE and to a lower SNR for each DW image, decreasing the estimation certainty and quality. Ideally, a diffusion-weighted acquisition should achieve a trade-off between acquiring adequate b-values while minimizing the TE to maximize the SNR.

An illustrative acquisition technique that may be used to acquire diffusion-weighted images having multiple non-zero b-values is called Cube and SPhere (CUSP) acquisition. This technique combines aspects of a single-shell HARDI with images in an enclosing cube of constant TE. The enclosing cube of the shell is a cube of constant TE, in which gradients with higher b-values can be imaged without increasing the TE, by using gradients with norm greater than one. Such an acquisition technique satisfies the requirement for multiple non-zero b-values, enabling the estimation of the complete multi-tensor model. High b-values may also be incorporated to allow for better characterization of multi-compartment models. In accordance with the techniques described herein, images associated with b-values higher than the nominal b-value may be acquired while achieving the same low TE as a single-shell HARDI. Compared to a multi-shell HARDI, CUSP acquisition results in a significantly higher SNR, shorter imaging time and potentially lower eddy current distortion than previously reported acquisition techniques.

The CUSP acquisition technique acquires multiple non-zero b-values by combining a first set of gradients for a single-shell HARDI acquisition at a specified $b_{nominal}$ (e.g., 1000 s/mm$^2$) with a second set of gradients having one or more different b-values and having associated gradient strengths that cause the gradients to lie within an enclosing cube of the inner shell. For example, the first set of gradients for the single-shell HARDI may uniformly sample the diffusion signal on the hemisphere, which is described by unit-norm gradients $\|g_k\|=1$. This inner shell employs the b-value providing the desired "optimal" SNR for the diffusion weighted acquisition.

The b-value for the inner shell may be determined by $b_{optimal}=1.11/ADC$, where ADC is the apparent diffusion coefficient of the tissue being imaged. An illustrative, non-limiting value for specified $b_{nominal}=b_{optimal}=1000$ s/mm$^2$ for an adult brain and $b_{optimal}=800$ s/mm$^2$ for a pediatric brain. The single-shell HARDI provides a full spherical sampling with the desired SNR and TE for the b-value $b_{nominal}$. A second set of gradient vectors may be specified to acquire additional b-values $b_k=b_{nominal}\|g_k\|^2$ without modifying the TE by modulation of $b_{nominal}$ with gradients whose strengths are greater than one: $\|g_k\|>1$.

The only constraint for $g_k$ is to have unit norm components, corresponding to the normalized current intensity in each gradient coil. Denoting the gradient components by $g_k=[g_k^X, g_k^Y, g_k^Z]^T$, this leads to $|g_k^X|\leq|g_k^Y|\leq|g_k^Z|\leq 1$, which describes the enclosing cube of the sphere of radius $\|g_k\|=1$, which is also referred to herein as the "cube of constant TE." Any gradient in this region can be acquired without modifying the TE by selecting the appropriate gradient strength. Because the diffusion sensitivity is dependent on the square of the gradient norm, imaging in the cube of constant TE enables the acquisition of b-values up to $3b_{nominal}$. This maximum b-value is obtained when using the four non-symmetric 0-norm tetrahedral gradients extending to the corners of the cube of constant TE $$(|g_k^X|=|g_k^Y|=g_k^Z|=1).$$

In an illustrative process for determining a gradient encoding scheme for DW-MRI, diffusion gradient vectors are selected, wherein at least two of the diffusion gradient vectors are associated with different non-zero b-values. For example, the diffusion gradient vectors for the gradient encoding scheme may include a first set of diffusion gradient vectors corresponding to a single-shell HARDI acquisition each having a b-value of $b_{nominal}$ and a second set (e.g., one or more) of diffusion gradient vectors each being associated a b-value different than $b_{nominal}$.

The gradient strengths for each of the diffusion gradient vectors may then be determined. As discussed above, in some embodiments, the plurality of diffusion vectors in the gradient encoding scheme may include a first set of diffusion gradient vectors corresponding to a single-shell HARDI acquisition. Each of the gradient vectors in the first set may have an identical gradient strength $\|g_k\|=1$ as they all fall on the surface of the sphere having a radius that corresponds to $b_{nominal}$. In contrast, the gradient strengths of the gradient vectors in the second set may be determined in any suitable way, with the only constraint that all of the vectors in the second set fall on or inside of the cube of constant TE.

Having defined all of the gradient orientations and gradient strengths in the gradient encoding scheme, the gradient encoding scheme may be used to acquire diffusion-weighted measurements. For example, an MRI system may be programmed with the determined gradient encoding scheme to control various components of the device to acquire diffusion-weighted images having multiple non-zero b-values. The diffusion-weighted measurements may then be used to approximate one or more diffusion-based parameters in a parametric model, as described above.

Figure 12:
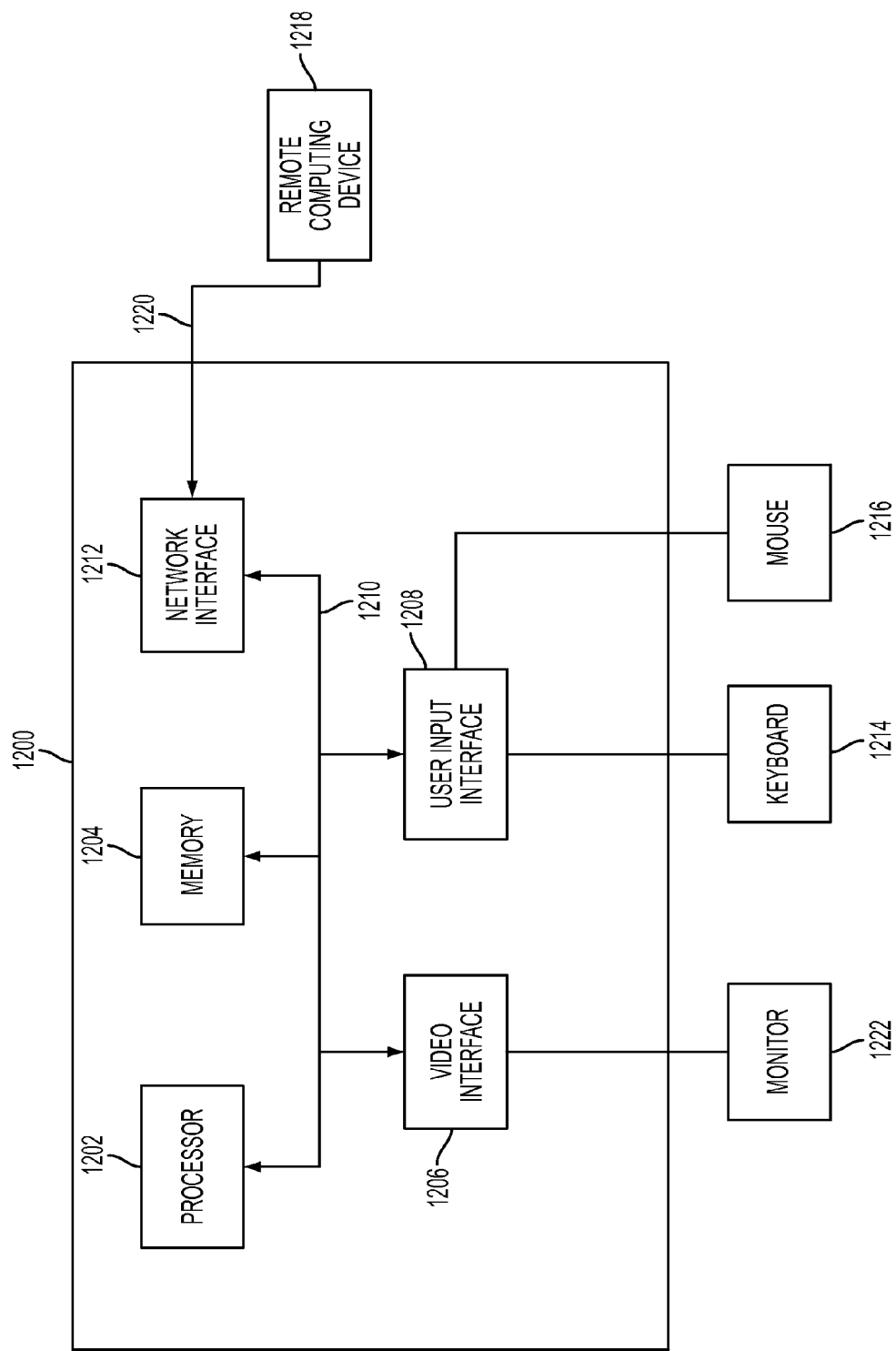
FIG. 12 is an exemplary computer system on which some embodiments may be implemented.

FIG. 12 shows a schematic block diagram of an illustrative computer 1200 on which features may be implemented. Only illustrative portions of the computer 1200 are identified for purposes of clarity and not to limit aspects of the invention in any way. For example, the computer 1200 may include one or more additional volatile or non-volatile memories, one or more additional processors, any other user input devices, and any suitable software or other instructions that may be executed by the computer 1200 so as to perform the function described herein.

In the illustrative embodiment, the computer 1200 includes a system bus 1210, to allow communication between a central processing unit 1202, a memory 1204, a video interface 1206, a user input interface 1208, and a network interface 1212. The network interface 1212 may be connected via network connection 1220 to at least one remote computing device 1218. Peripherals such as a monitor 1222, a keyboard 1214, and a mouse 1216, in addition to other user input/output devices may also be included in the computer system, as embodiments are not limited in this respect.

Figure 13:
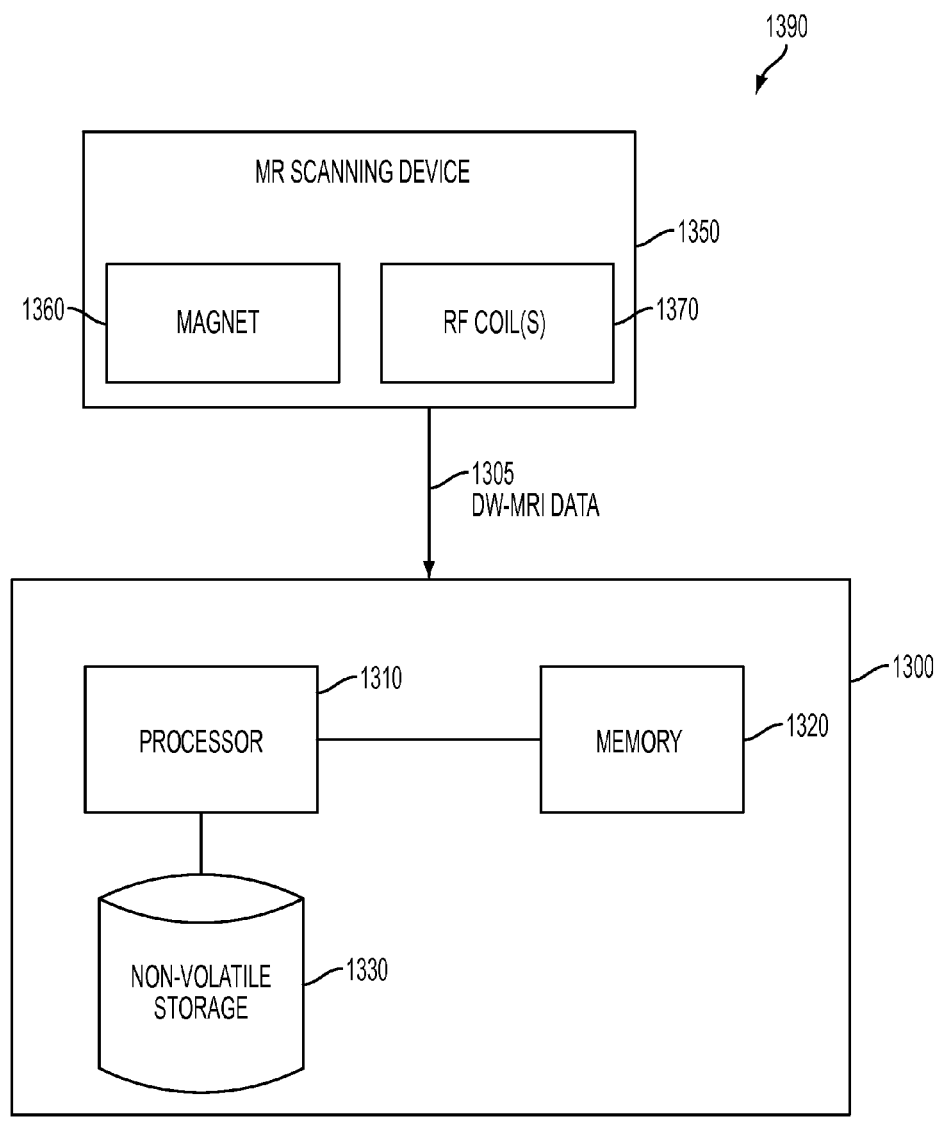
FIG. 13 illustrates a MR scanning device suitable for obtaining DW-MRI data in accordance with some embodiments.

FIG. 13 illustrates a block diagram of one embodiment of a system 1390 suitable for practicing various techniques described herein. System 1390 comprises a magnetic resonance (MR) scanning device 1350 and computer system 1300. MR scanning device 1350 may be any device capable of obtaining MR data and, in particular, capable of acquiring DW-MRI data. For example, MR scanning device 1350 may include a magnet 1360 capable of producing a magnetic field of desired strength, and may produce a uniform or gradient magnetic field. Magnet 1360 may be of any shape, size and strength and may include multiple magnets of any size, shape and strength.

MR scanning device 1350 also comprises one or more RF coils 1370 arranged proximate the magnet and adapted to provide RF pulse sequences to an object being scanned and/or to detect NMR signals (e.g., DW-MRI signals) emitted therefrom. RF coils 1370 may comprise one or multiple coils arranged in any configuration to perform single coil acquisition or multiple coil acquisition (i.e., parallel MR). RF coils 1370 may include independent RF coils for providing RF pulse sequences (excitation coils) and detecting NMR signals (receive coils), or one or more RF coils may be arranged as both an excitation and receive coils. Any configuration of magnet 1360 and RF coil(s) 1370 may be suitable, as the techniques described herein are not limited for use on data obtained from any particular MR scanning device.

Computer system 1300 may be used to implement one or more techniques described herein. Computer system 1300 may include one or more processors 1310 and one or more non-transitory computer-readable storage media (e.g., memory 1320 and one or more non-volatile storage media 1330). The processor 1310 may control writing data to and reading data from the memory 1320 and the non-volatile storage device 1330 in any suitable manner. Processor 1310, for example, may be a processor on any device, for example, a personal computer, a workstation, one or more servers, or may be a processor on-board or otherwise integrated with MR scanning device 1350, etc.

To perform functionality and/or techniques described herein, the processor(s) 1310 may execute one or more instructions stored in one or more computer-readable storage media (e.g., the memory 1320, storage media, etc.), which may serve as non-transitory computer-readable storage media storing instructions for execution by processor(s) 1310. Computer system 1300 may also include any other processor, controller, or control unit needed to route data, perform computations, perform I/O functionality, etc. For example, computer system 1300 may include any number and type of input functionality to receive data and/or may include any number and type of output functionality to provide data, and may include control apparatus to perform I/O functionality.

Computer system 1300 may be integrated into MR scanning device 1350 or may be a separate stand-alone computer system, either proximate to or remote from MR scanning device 1350. For example, computer system 1300 may be connected to MR scanning device 1350 over a network, connected to multiple scanning devices or may not be connected to any scanning device at all. When computer system 1300 is connected to or integrated with MR scanning device 1350, computer system 1300 may be programmed to control the RF coil(s) according to a desired RF sequence or protocol, or MR scanning device 1350 may have a separate controller to perform excitation and acquisition.

When computer system 1300 is separate from MR scanning device 1350, computer system 1300 may operate on MR data (e.g., DW-MRI data) previously stored on computer system 1300, may obtain DW-MRI data from some other location, e.g., another computer system, over a network, or may obtain the DW-MRI data via transportable storage medium, etc. It should be appreciated that any computing environment may be used, as the techniques described herein are not limited for use with a computer system of any particular type or implementation.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Through, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, embodiments may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect of this embodiment, one or more computer programs that when executed perform methods of embodiments need not reside on a single computer or processor, but may be distributed in a modular fashion amongst a number of different computers or processors to implement various embodiments.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationships between data elements.

Various aspects of embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

The invention claimed is:

1. A computer system for characterizing biological microstructure in a voxel based, at least in part, on a set of diffusion-weighted magnetic resonance (MR) data, the computer system comprising:
   a magnetic resonance imaging system;
   at least one computer processor; and
   at least one storage device configured to store a plurality of instructions that, when executed by the at least one computer processor, perform a method, comprising:
      controlling the magnetic resonance imaging system to acquire a set of diffusion-weighted MR data, wherein at least one first dataset of the set of diffusion-weighted MR data is associated with a first non-zero b-value and at least one second dataset of the set of diffusion-weighted MR data is associated with a second non-zero b-value different than the first non-zero b-value;
      fitting a parametric model using information from the set of diffusion-weighted MR data, wherein the parametric model is a multi-compartment model that includes a statistical distribution of diffusion tensors for each compartment of the multi-compartment model, and wherein fitting the parametric model comprises determining for the voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model; and
      outputting an indication of the first set of parameters and/or the second set of parameters for the voxel.

2. The computer system of claim 1, wherein the second set of parameters describe restrictive anisotropic diffusion in the second compartment.

3. The computer system of claim 1, wherein fitting the parametric model further comprises determining a third set of parameters describing hindered anisotropic diffusion in a third compartment, and wherein the method further comprises outputting the third set of parameters for the voxel.

4. The computer system of claim 1, wherein fitting the parametric model further comprises determining how many compartments to include in the multi-compartment model for the voxel based, at least in part, on the information from the set of diffusion-weighted MR data.

5. The computer system of claim 1, wherein the multi-compartment model includes at least four compartments, wherein the at least four compartments include a restricted isotropic diffusion compartment, a free isotropic diffusion compartment, a restrictive anisotropic diffusion compartment, and a hindered anisotropic diffusion compartment.

6. The computer system of claim 1, wherein the parametric model is DIAMOND.

7. The computer system of claim 1, wherein fitting the parametric model further comprises iteratively increasing the complexity of the parametric model until it is determined that further increases in complexity do not provide a statistically significant increase in the parametric model's ability to predict diffusion data in the voxel.

8. A method of characterizing biological microstructure in a voxel based, at least in part, on a set of diffusion-weighted magnetic resonance (MR) data, the method comprising:
   acquiring, using a magnetic resonance imaging system, a set of diffusion-weighted MR data, wherein at least one first dataset of the set of diffusion-weighted MR data is associated with a first non-zero b-value and at least one second dataset of the set of diffusion-weighted MR data is associated with a second non-zero b-value different than the first non-zero b-value;
   fitting a parametric model using information from the set of diffusion-weighted MR data, wherein the parametric model is a multi-compartment model that includes a statistical distribution of diffusion tensors for each compartment of the multi-compartment model, and wherein fitting the parametric model comprises determining for the voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model; and outputting an indication of the first set of parameters and/or the second set of parameters for the voxel.

9. The method of claim 8, wherein fitting the parametric model further comprises determining how many compartments to include in the multi-compartment model for the voxel based, at least in part, on the information from the set of diffusion-weighted MR data.

10. The method of claim 8, wherein the multi-compartment model includes at least four compartments, wherein the at least four compartments include a restricted isotropic diffusion compartment, a free isotropic diffusion compartment, a restrictive anisotropic diffusion compartment, and a hindered anisotropic diffusion compartment.

11. A non-transitory computer readable storage medium encoded with a plurality of instructions that, when executed by at least one computer processor, perform a method comprising:

acquiring, using a magnetic resonance imaging system, a set of diffusion-weighted MR data, wherein at least one first dataset of the set of diffusion-weighted MR data is associated with a first non-zero b-value and at least one second dataset of the set of diffusion-weighted MR data is associated with a second non-zero b-value different than the first non-zero b-value;

fitting a parametric model using information from the set of diffusion-weighted MR data, wherein the parametric model is a multi-compartment model that includes a statistical distribution of diffusion tensors for each compartment of the multi-compartment model, and wherein fitting the parametric model comprises determining for a voxel, based on the set of diffusion-weighted MR data, a first set of parameters describing isotropic diffusion in a first compartment of the multi-compartment model and a second set of parameters describing anisotropic diffusion due to the presence of at least one white matter fascicle in a second compartment of the multi-compartment model; and outputting an indication of the first set of parameters and/or the second set of parameters for the voxel.

12. The non-transitory computer-readable storage medium of claim 11, wherein the second set of parameters describe restrictive anisotropic diffusion in the second compartment.

13. The non-transitory computer-readable storage medium of claim 11, wherein fitting the parametric model further comprises determining a third set of parameters describing hindered anisotropic diffusion in a third compartment, and wherein the method further comprises outputting the third set of parameters for the voxel.

14. The non-transitory computer-readable storage medium of claim 11, wherein fitting the parametric model further comprises determining how many compartments to include in the multi-compartment model for the voxel based, at least in part, on the information from the set of diffusion-weighted MR data.

15. The non-transitory computer-readable storage medium of claim 11, wherein the multi-compartment model includes at least four compartments, wherein the at least four compartments include a restricted isotropic diffusion compartment, a free isotropic diffusion compartment, a restrictive anisotropic diffusion compartment, and a hindered anisotropic diffusion compartment.

16. The non-transitory computer-readable storage medium of claim 11, wherein fitting the parametric model further comprises iteratively increasing the complexity of the parametric model until it is determined that further increases in complexity do not provide a statistically significant increase in the parametric model's ability to predict diffusion data in the voxel.

* * * * *

UNITED STATES PATENT AND TRADEMARK OFFICE
CERTIFICATE OF CORRECTION

| | | |
|---|---|---|
| PATENT NO. | : 10,317,498 B2 | Page 1 of 1 |
| APPLICATION NO. | : 15/022343 | |
| DATED | : June 11, 2019 | |
| INVENTOR(S) | : Simon K. Warfield et al. | |

It is certified that error appears in the above-identified patent and that said Letters Patent is hereby corrected as shown below:

In the Specification

At Column 1, Line 18, below the RELATED APPLICATIONS paragraph, please add the following new paragraph:
FEDERALLY SPONSORED RESEARCH
This invention was made with government support under Grant Numbers NS079788, EB013248, LM010033, and MH086984, awarded by the National Institutes of Health. The Government has certain rights in the invention.

Signed and Sealed this
Twenty-second Day of November, 2022

*Katherine Kelly Vidal*

Katherine Kelly Vidal
*Director of the United States Patent and Trademark Office*